United States Patent
Froehlich et al.

(10) Patent No.: US 9,630,026 B2
(45) Date of Patent: Apr. 25, 2017

(54) NON-PLANAR TREATMENT BEAM CONTROL

(75) Inventors: Stephan Froehlich, Aschheim (DE); Franz Gum, Munich (DE); Kajetan Berlinger, Munich (DE)

(73) Assignee: Brainlab AG, Munich (DE)

( * ) Notice: Subject to any disclaimer, the term of this patent is extended or adjusted under 35 U.S.C. 154(b) by 345 days.

(21) Appl. No.: 13/811,294

(22) PCT Filed: Jul. 23, 2010

(86) PCT No.: PCT/EP2010/060710
§ 371 (c)(1),
(2), (4) Date: Jan. 21, 2013

(87) PCT Pub. No.: WO2012/010215
PCT Pub. Date: Jan. 26, 2012

(65) Prior Publication Data
US 2013/0131430 A1    May 23, 2013

(51) Int. Cl.
*A61N 5/10* (2006.01)

(52) U.S. Cl.
CPC ............. *A61N 5/1049* (2013.01); *A61N 5/10* (2013.01); *A61N 5/103* (2013.01); *A61N 5/1042* (2013.01); *A61N 5/1082* (2013.01)

(58) Field of Classification Search
CPC .... A61N 5/103–5/1039; A61N 5/1041; A61N 5/1043; A61N 5/1077;
(Continued)

(56) References Cited

U.S. PATENT DOCUMENTS

2004/0005027 A1 * 1/2004 Nafstadius ........... A61N 5/1049
378/65
2004/0184579 A1 * 9/2004 Mihara .................... A61N 5/10
378/65
(Continued)

FOREIGN PATENT DOCUMENTS

EP    1419799    8/2002
EP    1419801    3/2003
(Continued)

OTHER PUBLICATIONS

International Search Report for International Application No. PCT/EP2010/060710 dated May 10, 2011.
(Continued)

*Primary Examiner* — Catherine B Kuhlman
(74) *Attorney, Agent, or Firm* — Tucker Ellis LLP

(57) ABSTRACT

The present invention relates to a data processing method for determining control data for controlling beam positions which beam positions describe positions which a treatment beam has or would have if emitted by a beam source, the treatment beam being for treating a treatment body part of a patient, said method constituted to be performed by a computer and comprising the steps of: • providing treatment data which comprise data on a position of the treatment body part; • providing condition data which describe: constraints on the beam positions and/or constraints on positional changes of the beam positions, wherein said constraints allow for at least a part of the beam positions to lie not in a common plane; • providing an arrangement of the beam positions on the basis of the treatment data which arrangement fulfils the condition data; • determining control data for controlling a change of a relative position of the beam source relative to the treatment body part for changing the beam positions and for controlling an emission of the treatment beam from the beam source, the determined control data
(Continued)

being constituted to change the beam positions to follow the provided arrangement of the beam positions and to cause continuous emission of the treatment beam during a continuous change of the beam positions while the beam positions follow at least a part of the arrangement.

15 Claims, 5 Drawing Sheets

(58) Field of Classification Search
CPC .................. A61N 5/1081–5/1082; A61N 2005/1032–2005/1041; A61N 5/1047
See application file for complete search history.

(56) References Cited

U.S. PATENT DOCUMENTS

2007/0016014 A1* 1/2007 Hara et al. .................. 378/65
2008/0298550 A1* 12/2008 Otto .............................. 378/65

FOREIGN PATENT DOCUMENTS

| | | |
|---|---|---|
| EP | 1 419 799 A1 | 5/2004 |
| EP | 1 419 801 A1 | 5/2004 |
| WO | 00/74779 A1 | 12/2000 |
| WO | 0074779 | 12/2000 |
| WO | 2004/004829 A1 | 1/2004 |
| WO | 2004004829 | 1/2004 |
| WO | 2008/039991 A1 | 4/2008 |
| WO | 2008039991 | 4/2008 |
| WO | 2008/130634 A1 | 10/2008 |
| WO | 2008130634 | 10/2008 |

OTHER PUBLICATIONS

Office Action (5 pgs) dated: Jun. 19, 2015 for application No. 10737038.9-1652; European Patent Office, Munich, Germany.
European Patent Office, Substantive Examination for EP10737038.9, Jul. 7, 2016, pp. 1-4.

* cited by examiner

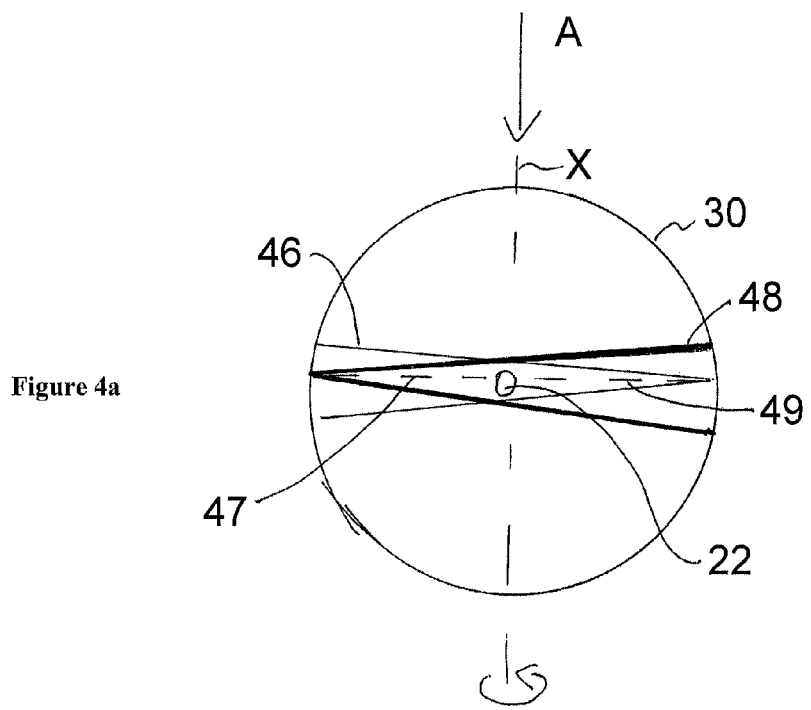
Figure 4a
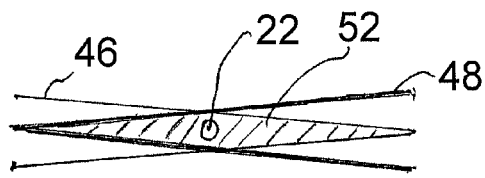
Figure 4b
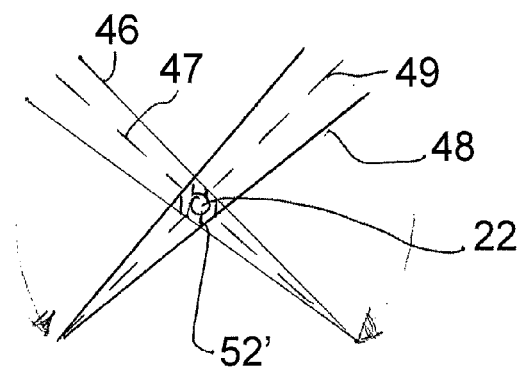
Figure 4c
Figure 4

NON-PLANAR TREATMENT BEAM CONTROL

This application is a national phase of International Application No. PCT/EP2010/060710 filed Jul. 23, 2010 and published in the English language.

The present invention relates to the field of controlling a treatment beam. The treatment beam treats body parts to be treated, which are referred to in the following as "treatment body parts". These body parts are in particular parts of a patient's body, i.e. anatomical body parts.

The present invention relates to the field of medicine and in particular to the use of beams, in particular radiation beams (referred to as "treatment beams"), in order to treat parts of the body. Ionising radiation is in particular used for this purpose. In particular, the treatment beam comprises or consists of radiation, in particular ionising radiation. The ionising radiation comprises or consists of particles (for example sub-atomic particles or ions) or electromagnetic waves which are energetic enough to detach electrons from atoms or molecules and so ionise them. The treatment beam is in particular used in medical therapy, in particular in radiation therapy (radiotherapy), in particular in the field of oncology. For the treatment of cancer in particular, the parts of the body comprising the tumour are treated using ionising radiation. The tumour is an example of a treatment body part. In particular, the treatment body part absorbs a part of the radiation of the treatment beam in order to achieve the desired medical effect. Thus, there is a (desired) radiation exposure of the treatment body part.

The treatment beam is preferably controlled so as to pass through a target volume (target region) filled by the treatment body part. However, the treatment beam can have a negative effect on body parts outside of the treatment body part. Such body parts are referred to here as "outside body parts" which fill a non-target volume. Generally, a treatment beam has to pass through at least some of the outside body parts in order to reach and so pass through the treatment body part. Those outside body parts through which the treatment beam passes fill a region called herein exposed outside region.

With respect to background information, reference is made to products by Elekta and Varian Medical Systems.

It is an object of the invention to effectively treat a treatment body part, wherein negative effects on outside body parts are advantageously reduced and the treatment time is advantageously short.

The aforementioned object is solved by the subject-matter of the independent claims. The dependent claims are directed to advantageous embodiments.

In the following further advantages, advantageous optional features and advantageous embodiments of the invention are described. Generally, different advantageous embodiments as described herein and individual features of said advantageous embodiments can be combined with other advantageous embodiments or their features.

In accordance with an advantageous embodiment of the present invention, a treatment is planned or performed by determining control data for controlling the beam positions of the treatment beam so as to follow a particular arrangement if a beam source (continuously) emits the treatment beam. The arrangement is an arrangement of a plurality of beam positions, in particular a discrete set of beam positions or a continuous multiplicity (in particular manifold) of beam positions which is determined in accordance with the invention on the basis of condition data. The arrangement of beam positions is in particular an arrangement of beam positions provided by the data processing method. Therefore the arrangement can also be called an arrangement of provided beam positions (or planned beam positions). The provided beam positions have to fulfil the conditions, in particular the constraints on the beam positions. Preferably, the control data are for controlling the relative movement of the beam source relative to the treatment body part which control changes the beam positions, the change being in line with the provided arrangement of the (provided) beam positions. Preferably, the beam positions defined by the relative positions of the beam source (also called "actual beam positions") follow arrangement, in particular the provided (planned) beam positions which constitute the arrangement. The term "follow" means that the control data are constituted to effect that the actual beam positions are continuously changed to wander along the surface spanned by the provided arrangement of planned beam positions, in particular in accordance with a continuous forward movement (from a starting edge of the provided arrangement to an ending edge of the provided arrangement) and an optional backward movement. "Follow" in particular means to sequentially adopt the positions of neighbouring provided beam positions. An at least partly continuous emission during the change of the beam positions encompasses in particular a (fully) continuous emission as well as a continuous emission with interruptions, i.e. an intermittent emission. The intermittent emission comprises extended intervals of continuous emission (in particular larger than 1 s or 10 s) in particular during which there is a continuous change of the beam positions achieved by a relative movement of the beam source along an extended section of the beam source path (e.g. longer than 1 cm or 10 cm). Preferably, at least one of these extended sections is a curved section along a curved part of the spanned surface. The discrete set of beam positions can define and in particular span a surface, in particular a curved surface. The continuous multiplicity (in particular manifold) of beam positions can define and in particular span a surface (in particular represent the surface), in particular a curved surface. A curved surface is a surface of which at least one part is curved (i.e. the curvature of the curved part is not equal to zero). Preferably, there is at least a continuous emission of the (active) treatment beam while the treatment beam follows the at least one curved part of the curved surface or at least one of the curved parts. The determination step is also designed to allow the arrangement to be non-planar. Both the at least intermittently continuous emission of the (active) treatment beam while it is following (at least a part of) the arrangement and the ability of the determination step to allow for a non-planar arrangement enables a short treatment time, while keeping the radiation exposure of at least some of the outside body parts low as will be explained in more detail below.

Preferably, the determined control data are constituted to control a relative position between the treatment body part and the beam source so that the treatment beam continuously follows the arrangement during a continuous emission of the treatment beam from the beam source. Preferably, the control data result in a continuous change of the relative position between the beam source and the treatment body part in a manner that the (active) treatment beam follows the surface defined by the determined arrangement or that the treatment beam (which is inactive) would follow the determined arrangement if the treatment beam were activated. The control data can further comprise data for controlling the emission of the treatment beam from the beam source, in particular an on and off status of emission of the beam source, in particular intensity and/or shape of the treatment beam emitted by the beam source. In particular the emission of the treatment beam from the beam source can be interrupted during the continuous movement of the beam source relative to the treatment body part in accordance with the control data. This can be used in order to avoid a damage of special outside body parts due to the treatment beam. To this end, also the intensity of the treatment beam can be varied, in particular reduced when the treatment beam passes through special outside body parts. As will be explained in more detail later, particular advantage of the invention is, that the arrangement can be determined so that the radiation exposure of outside body parts, in particular of special body parts is reduced.

The radiation exposure in a body part (e.g. treatment body part, outside body part, spe'cial outside body part) represents in particular the radiation absorbed by the body part due to the effect of the treatment beam. The radiation exposure can be described by a radiation dose (also called herein treatment dose), can be described by energy per mass unit (kg) which is absorbed by the body part, can be described by energy per volume which is absorbed by the body part and can be described by a portion (in particular percentage) of the volume which is subjected to the radiation, and can be described by a portion (percentage) of the volume of the body part within which the absorbed radiation (in particular radiation dose) is lower and/or higher than a predefined level.

In accordance with an advantageous embodiment, treatment data are provided which comprise data on a position and/or geometry of the treatment body part. That is data on a position and/or geometry of a region (treatment region) filled by the treatment body part. Preferably, the treatment data describe the position of the treatment body part relative to at least one of the following: a reference system in which one of the possible positions of the beam source and/or a center of movement of the beam source (in particular an isocenter of rotation) is at rest; a reference system in which the treatment body part is at rest; a reference system in which a treatment plane is at rest; the determined arrangement of the beam positions; at least one of the possible beam positions; an averaged position of the possible beam positions; the room in which the radiation treatment system is located; a non-movable part of a support structure which supports the beam source, etc. The treatment data are designed to allow a relative position between the treatment beam and the treatment body part to be determined. Preferably, the position of the treatment body part and the position of the determined arrangement of beam positions is described in a reference system in which both the treatment body and the arrangement lie. In particular, the treatment data describe the geometry (size and/or shape) of the treatment body part.

In this document, the term "position" comprises the meaning of "location", as described for example by spatial co-ordinates, and/or "orientation", in particular for example a rotational alignment.

Preferably, the step of providing treatment data involves receiving treatment data, in particular via a computer interface. Preferably, the received treatment data are generated by means of an analysis apparatus such as an x-ray device, MRT or CT. The analysis apparatus allows to determine (in particular to monitor) the position of the patient, in particular the position of the treatment body part. To this end, two-dimensional images (for example, x-ray images) acquired during treatment can in particular be matched to three-dimensional images (for example, CT or MRT images) before treatment, in particular the two and/or three dimensional images can be used for determining the position of the treatment body part (as is described in the following applications):

EP 01 124 379.7
EP 02 028 015.2
EP 08 156 293.6
EP 07 150 014.4
EP 09 157 950.8
EP 09 159 002.6
EP 08 169 422.6
EP 09 160 153.4
PCT/EP2010/052619
EP 10 156 016.7
U.S. Ser. No. 12/333,556
U.S. Ser. No. 12/760,575
U.S. Ser. No. 12/769,971
U.S. Ser. No. 12/621,881
U.S. Ser. No. 12/622,002

Preferably, condition data are provided which describe conditions. Said conditions in particular include radiation exposure conditions, in particular a condition regarding the radiation exposure in outside body parts, in particular a condition that the radiation exposure of outside body parts has to be lower than a predefined level and/or the radiation exposure of the treatment body part has to be higher than a predefined level. In particular, the radiation exposure in outside body parts is minimized. As mentioned above, "outside body parts" are located outside the treatment body part. Preferably, at least some of the outside body parts (in particular so called special outside body parts) are not subjected to the treatment beam or are only subjected to a low radiation exposure. In accordance with the invention, this is achieved in particular by moving the treatment beam. In some prior-art solutions, the position of the treatment beam is static. This results in a higher radiation exposure in those outside body parts through which the treatment beam passes. By contrast, if the treatment beam is moving, the local radiation exposure is reduced. Since, however, the treatment beam preferably passes through the treatment body part during the movements, the radiation exposure in the treatment body part is high, while the energy of the treatment beam is spread over a larger volume of outside body parts (in particular by increasing the exposed outside region). This results in a reduced average (mean) radiation exposure (per volume) in those outside body parts through which the treatment beam passes. In particular, peaks of higher radiation exposures in some of the outside body parts are advantageously avoided. The condition data, in particular the radiation exposure condition, preferably describe the position and/or geometry (size and/or shape) of the outside body parts. By determining the overlap between a region filled by the determined arrangement of treatment beams and a region filled by the outside body parts, it is possible to determine the position and/or geometry of those outside body parts ("exposed outside body parts") which are subjected to the radiation and thus to determine the region (called "exposed outside region") which is subjected to radiation. In particular, the radiation exposure (in particular the local maximum radiation exposure) is preferably reduced for the exposed outside region (in a way described below) which is filled by the exposed outside body parts. In accordance with another embodiment, the condition data describe (alternatively or additionally) the position and/or geometry of the treatment body part. The position and geometry of the exposed outside region is determined on the basis of the known position and geometry of the treatment body part (i.e. the treatment region) to be that region which is exposed to radiation and outside the treatment body part but inside the body of the patient.

In accordance with another advantageous embodiment, the condition data include a radiation exposure condition, according to which the volume of a part of the exposed outside region within which the radiation exposure is higher than in the remaining part of the exposed outside region has to be minimised and/or has to be below a certain percentage such as for example 30%, 20%, 10%, 5% or 1%. In particular, the condition is that the volume of a part of the exposed outside region which is subjected to the treatment beam two or more times is minimised and/or below the above-mentioned percentage. The aforementioned radiation exposure condition is therefore also called "no-double-pass condition". An example for a no-double-pass condition is also a condition which has as a consequence that the volume of the exposed outside region through which the treatment beam passes more than once is minimized or below a certain percentage. An example will be given below.

The conditions described by the condition data preferably also include radiation exposure conditions which in particular include a condition regarding the radiation exposure in the treatment body part, in particular a condition for the radiation exposure (or a range of radiation exposure) inside the treatment body part which generally has to be higher than in outside body parts. As mentioned above, this is preferably achieved by moving the treatment beam so that the treatment beam passes through the treatment body part from different directions. Thus, the treatment body part is continuously irradiated by the treatment beam, while the treatment beam changes its position (in particular its orientation) relative to the treatment body part. The inventors of the present invention have found that the radiation exposure in outside body parts can be reduced if the treatment beam is allowed to leave a plane during the treatment of the treatment body part while still passing through the treatment body part. In particular, it is possible to reduce the volume of outside body parts having to endure a higher dose than other outside body parts and/or to spare specific outside body parts the burden of the radiation exposure. In particular by leaving the plane, the volume of the exposed outside region is increased compared to the case of not leaving the plane. Thus, also reducing the (average) radiation exposure per mass or volume. Thus, in accordance with the invention, the arrangement of the beam positions is preferably determined in a way which allows the arrangement of the beam positions to be non-planar.

Preferably, the arrangement is provided on the basis of the treatment data and the condition data, i.e. the arrangement is in particular provided in accordance with the treatment data and the condition data. The provision of the arrangements can be performed based on user inputs (that is data input by the user). Based on the received user inputs, the arrangement of the beam positions is determined by the data processing method. For instance, beam positions can be inputted by a user which reflect that particular outside body parts are to be avoided. In particular, the received (discrete) (beam positions are interpolated (for instance by a spline function) in order to determine the arrangement. According to another embodiment, for instance an optimizer is used in order to automatically determine an arrangement which optimally fulfils the exposure radiation conditions. Providing the arrangement based on the treatment data comprises in particular the step that an arrangement determined based on received user inputs is checked whether if the beam positions pass through the treatment body part or the beam positions determined based on the user input are automatically changed so that they pass through the treatment body part. Providing the arrangement of beam positions based on the condition data comprises in particular the step that the arrangement based on user input is rejected if the condition data are not fulfilled or that the arrangement determined based on user inputs is changed (adapted) so that the condition data are fulfilled. If for instance the arrangement based on user input shows (a curvature of) a surface spanned by the arrangement which is not in line with the constraints on positional changes of the treatment beam (in particular allowed movements of the beam source), then the arrangement is adapted to be in line with the constraints or the user is warned and/or prompted to make a new input based on which a new arrangement can be determined. In case of a change, preferably, the changed arrangement is shown to the user on a screen.

Preferably, the radiation exposure of body parts (outside body parts, special outside body parts and/or treatment body parts) given for an arrangement is shown on the screen. The user can then accept the proposed arrangement. Thus, the data processing method receives an acceptance signal from the user. In this way, finally the arrangement of beam positions is provided (determined) by the data processing method and the control data are determined based on the provided arrangement by the data processing method in a next step.

The provision of the arrangement of beam position is in particular performed by using an optimization algorithm. The optimization algorithm is in particular a numerical method. In the present case, the optimization algorithm is in particular used to (automatically) find an arrangement of beam positions which optimally fulfils the conditions. In particular, the optimization algorithm is used to determine an arrangement which optimally fulfils at least one of the radiation exposure conditions while still fulfilling the constraints on the positions of the treatment beam and/or the constraints on the positional changes of the treatment beam. The optimization algorithm can be also used in a semiautomatic environment in which for instance some of the beam positions are received (e.g. by user input) and the reminder of the arrangement is determined by using the optimization algorithm which has in particular the additional constraint that the arrangement has to comprise the received beam positions.

According to a further embodiment, the arrangement is received (e.g. by user input) and the received arrangement is optimized by using the optimization algorithm. In particular the received arrangement is used as a starting point for the optimization algorithm. In particular, the optimization algorithm adapts the arrangement (e.g. changes curvatures of the surface spent by the arrangement) in order to optimize the fulfillment of the conditions (in particular radiation conditions and positional constraints on the positions of the treatment beam and on positional changes of the treatment beam).

Control data are also preferably determined. In particular, the determined control data are outputted by the data processing method. The control data are in particular constituted to control a relative position of the beam source (which issues the treatment beam) relative to the treatment body part so that the treatment beam (at least partly continuously) follows the arrangement of beam positions if the beam source is active, i.e. (at least partly continuously) emits the treatment beam. The relative position of the beam source relative to the treatment body part can be for instance changed by moving the beam source or by moving the treatment body part, in particular by moving the patient (for instance by moving a couch on which the patient is lying). Both movements (movement of beam source and movement of patient) can be combined. In particular, control data are constituted such that they are able to cause that the relative position is at least partly continuously changed during treatment of the patient while the beam source can be active (on state) or inactive (off state) during the at least partly continuous change of the relative position. Thus, the active treatment beam can intermittently follow the arrangement of beam positions if the beam source is switched on and off. Thus the beam source emits at least during a part (in particular section or time interval) of its (in particular continuous) movement (during treatment) actively the treatment beam. The part being in particular at least 10%, 20% or 50% or 90% of the path of the beam source during treatment. Preferably, there is at least a continuous emission for at least one section of the beam source path (which section is for instance at least 1 cm or 10 cm long) while the beam source follows the arrangement. The aforementioned time interval of continuous movement and continuous emission is preferably at least 1 s or 10 s. The aforementioned part is in particular an extended part and not just a point (in time or space). The change of the (actual) beam positions for following the provided arrangement (during treatment) is at least partly a continuous change, i.e. can be (fully) continuous or intermittently. The intermittent change of the (actual) beam positions (i.e. an only partly continuous change) comprises extended intervals (e.g. larger than 1 s or 10 s) of continuous change of beam positions and at least one stop of movement. The control data are preferably determined so that there are at least extended intervals (e.g. larger than 1 s or 10 s) (during treatment and while following the arrangement) during which there is both a continuous change of beam position and an active emission of the treatment beam. Preferably, the sum of the interval represents more than 10%, 30%, 50%, 80% or 90% of the total time during which the beam positions are changed for following the arrangement. Preferably, the sum of beam source path sections during which there is both a continuous change of beam positions and an active emission of the treatment beam (while following the arrangement) represent more than 30%, 50%, 80% or 90% of the total beam source path (which the beam source follows during treatment, i.e. while the beam positions follow the arrangement). In particular during the interval of both continuous change of beam positions and continuous emission, the beam positions follow a curved part of the arrangement. Preferably, the relative positions is continuously changed in a manner that the treatment beam would follow the arrangement of beam positions if the beam source is activated (even if the beam source is inactive). In other words, even in the inactive status of the beam source, the control data are constituted to change the relative position between the treatment body part and the beam source in a manner that the treatment beam would follow continuously the arrangement of beam positions if the beam source were active. In other words, the control data define a continuous relative movement between the beam source and the treatment body part in accordance with the provided arrangement of beam positions. In particular, the control data are used to control the treatment beam. In particular the control data are used to control the position of the (active or inactive) beam positions and in particular to control the emission of the treatment beam, for instance the intensity of the treatment beam, for instance the "on" or "off" state of the treatment beam. In this document, the term "active treatment beam" is understood to mean that the treatment beam is active (i.e. in the "on" state), i.e. that a beam source emits the treatment beam which has a position called herein "active beam position". This means in other words, there is no emission of an inactive treatment beam but of course only of an active treatment beam according to the understanding of the present invention. The inactive beam position defines an orientation of the beam source relative to the treatment body part. In other words, the inactive beam positions describe the positions which the treatment beam would have if it were activated or still in other words, the inactive beam positions describe the positions of the "inactive treatment beam". In particular, the beam source is controlled to have the orientation relative to the treatment body part. The beam surface can be understood to be a multiplicity of beam lines, at least a part of these beam lines being active beam lines or in other words at least a part of the beam surface being active, i.e. being an active beam surface. The beam source emits the treatment beam when it follows the active part of the beam surface and does not emit a treatment beam when it follows one or more optional inactive parts of the beam surface. Preferably, the control data control the treatment beam (i.e. the active treatment beam and the inactive treatment beam) so as to continuously follow the determined arrangement of beam positions. Thus, the treatment body part is preferably at least intermittently irradiated continuously and from different directions. The directions preferably change continuously while the (active or inactive) treatment beam continuously changes its position relative to the treatment body part. Preferably, the positions of the active and inactive treatment beam can be represented by vectors which in particular do not lie in a common plane. The (active and inactive) treatment beam continuously changes its position during the treatment, while following a surface (also called beam surface) which represents a two-dimensional (continuous) path to be followed. The beam surface is defined and in particular spanned by the determined arrangement and is in particular a virtual surface.

In particular a surface (called herein treatment surface) is a sphere with its center being the center of the treatment body part. In particular the center of the treatment body part coincedes with the center of the relative movement of the beam source relative to the treatment body part. In particular this relative movement is a rotation of the beam source around the treatment body part. In particular, an intersection of the beam surface with the treatment surface is a one-dimensional continuous path and in particular the end positions of the beam positions spanning the beam surface and in the center of the treatment surface, i.e. in the treatment body part. The movement (of the beam source relative to the treatment body) can be achieved by moving the beam source by means of a beam source driving device and/or by moving the couch. The movement of the beam source is in particular described in a reference system in which the treatment body part is at rest.

The so called beam positions describe positions which a treatment beam has (active beam positions) or would have (inactive beam positions) if emitted by a beam source "during treatment". The term "during treatment" means in particular that the beam source is moving relative to the treatment body part and the time of treatment (i.e. "during treatment") is the time from the first emission of the treatment beam to the last emission of the treatment beam while the beam source is continuously moving from the first emission to the last emission of the treatment beam. The beam source can continuously emit from the first to the last emission or intermittently emit from the first to the last emission of the treatment beam.

The (active or inactive) "beam positions" describe the positions of the (active or inactive) treatment beam (in particular relative to the treatment body part) and can in particular describe a position of a (one-dimensional) line which represents the position of the (active or inactive) treatment beam and can pass through the centre of the treatment beam and is in particular aligned with the direction of the (active or inactive) treatment beam. This line is called the (active or inactive) "beam line" and is in particular a virtual line. In particular, (active or inactive) "treatment beams" are respectively assigned to the (active or inactive) "beam positions" (and vice versa) and to (active or inactive) beam lines. Beam positions are described here as spanning a (virtual) surface which represents the beam surface. This concept of a "virtual surface" is in particular used to define the geometry (size and/or shape) of the arrangement of beam positions. The virtual surface is in particular spanned by the beam lines representing the beam positions, in particular all of the beam positions. In particular, these beam lines start at the point from which the beam source emits (or would emit) the active (or inactive) treatment beam in the beam position. In order to describe the position and/or geometry of the arrangements, the (active or inactive) beam lines are in particular assumed to end at the treatment body part. The (active or inactive) beam lines which end in the treatment body part can have different orientations, in particular inclinations, in particular with respect to a plane which is in particular the treatment plane. The (active or inactive) beam lines in particular move within the spanned virtual surface while the (active or inactive) treatment beam changes its positions relative to the treatment body part. Thus, a multiplicity of beam lines can represent the spanned virtual surface. Due to a relative movement of the beam source from a path starting point to a path finishing point (while emitting or not emitting the treatment beam) relative to the treatment body part, the (active or inactive) beam positions continuously change relative to the treatment body part. Preferably, the beam source driving device is designed such that it can (but need not) move the beam source relative to the treatment body part such that all the beam positions (from the path starting point to the path finishing point) lie in a plane. Preferably, there are one or more of these planes, and one of these planes (for instance, the middle plane or an average plane) can be defined as the treatment plane.

Preferably the treatment plane is determined as follows. As mentioned above, the beam lines start at the point from which the beam source emits. These points are called "start points". The start points can lie in a plane or outside a plane. If the start points are outside of a plane, one of the start points has a maximum distance from the plane. At each side of the plane, there is one start point which has the maximum distance from the plane. Thus there are two maximum distances one for each side of the plane. The treatment plane is preferably selected so that these maximum distances are at least approximately equal. Alternatively or additionally, if there are local maxima of distance of start points from the plane, the treatment plane is preferably chosen so that the number of starting points which represents the local maxima of distance are about equal on both sides of the treatment plane. The aforementioned definitions of a treatment plane is just one of a number of possible definitions.

Preferably, the patient couch is adjusted such that the treatment plane passes through the treatment body part. The beams have a (three-dimensional) volume which the treatment beam fills when the beam source emits the treatment beam. The beam positions can also be considered to represent the position of this three-dimensional volume. In particular, each beam has a (beam) volume in its respective beam position. The shape of the treatment beam can be variable, as is known from so-called multi-leaf collimators (MLC). The volume of the determined arrangements can in particular be determined by combining the multitude (or multiplicity) of treatment beam volumes. The volume of the parts of the body subjected to treatment radiation is then the overlap between the volume of the arrangement and the volume of the body. The "outside body parts" as described here are preferably understood to be the parts which are within this overlap (but outside the treatment body part).

The conditions preferably include information (in particular constraints) on possible (active or inactive) beam positions of the (active or inactive) treatment beam (relative to the treatment body part) and/or on possible changes in the (active or inactive) beam position (relative to the treatment body part). These changes are also referred to as positional changes or relative positional changes and the beam positions are also referred to as relative beam positions. The term "possible" as used here refers in particular to constraints, in particular rules describing predetermined constraints (i.e. what is and/or is not allowed) and in particular ranges of beam positions relative to the treatment body part and/or ranges of vectors or velocities (e.g. angular velocities) which describe constraints on positional changes in beam position. These constraints are in particular based on constraints of the radiation treatment system, in particular mechanical and/or electrical constraints. There can for example be mechanical and/or electrical constraints on the beam source driving device which changes the position of the beam source in order to change the beam position, such as for example that only particular rotations about particular axes are allowed and/or that only particular ranges of rotational angles or angular velocities about an axis are allowed and/or that only particular translational movements are allowed. Other equipment of the radiation treatment system, such as for example the patient couch, can also have an influence on the allowed ranges of relative beam positions or of relative positional changes. For example particular ranges are allowed for positional changes of the couch or particular ranges of velocity or acceleration are allowed for positional changes of the couch. In particular, the driver of the beam source and a driver of the couch to change the relative position of the treatment beam relative to the treatment body part can cooperate even during radiation treatment to achieve the relative movement of the beam source relative to the treatment body part. In this way, the constraints are defined based on both the possible beam positions and positional changes of the beam source and the possible beam positions and positional changes of the couch. The constraints on the possible positions of the treatment beam and/or the possible positional changes in the treatment beam can also be preset by an operator, for instance due to safety considerations.

Advantageously, the possible positions and/or positional changes—which are preferably defined by the condition data—are preferably such that the beam positions do not all have to lie in a common plane. In particular, the constraints are such that a treatment beam can leave a plane within which the treatment beam has previously performed a continuous change in position. The possible positions and/or positional changes are in particular such that beam positions which lie in a curved surface are possible and/or changes in the beam position which are necessary in order to follow a curved surface are possible. The constraints on the positional changes in the treatment beam can in particular be due to physical conditions stipulated by the radiation treatment system (and/or can be preset as mentioned above). Such physical conditions relate in particular to the mass of the beam source and the driving power of the beam source driving device. In particular, the inertia of the beam source means that there is a continuous change in the beam position as the beam source is driven. In particular, there is a range or upper level for a (positive or negative) acceleration of the beam source. The acceleration can be described by a scalar or a vector. In particular, there can be a maximum or upper level for the allowed curvature of the surface which can be spanned by the arrangement of beam positions. In particular, the beam positions follow the curved (spanned) surface during movement and during treatment. In particular, the constraints are such that there is a continuous change in beam position while the treatment beam is active during treatment of a patient. In particular, there is a continuous change of (active or inactive) beam positions if the treatment beam is only intermittently active during treatment of a patient, i.e. there is at least one time interval during treatment during which the treatment beam is inactive while the treatment beam is in particular active before and after the at least one inactive interval. In particular there is at least one time interval during which the treatment beam is active and the beam source is moving relative to the treatment body part (in particular not in a plane but in a curved surface). In particular, the constraints are such that there is no interruption in movement of at least one of the beam source and the couch as the beam source is moved from a starting point to a finishing point. In particular, the constraints on the positions and positional changes (relative to the treatment body part) are such that not all the positions of the treatment beam have to be in a common plane. In particular, the constraints on the positions and/or positional changes, i.e. the possible positions and/or positional changes, are such that they can be reached by a continuous change in the position of the treatment beam, which is in particular caused by a continuous change in the position of the beam source (and/or the couch) during treatment of a patient. In particular, the constraints exclude particular beam positions and/or positional changes of beam positions while not excluding for at least some of the beam positions to lie not in a common (i.e. single) plane.

The constraints on the positions and/or positional changes can also be described by constraints on the control data for controlling the treatment beam. The condition data can for example be described by ranges of allowed (or excluded) control data corresponding to ranges of translational or rotational movements of the beam source. In particular, there can be rules for changing the control data which reflect the allowed (or excluded) positional changes in the beam source. These allowed (or excluded) positional changes in the beam source can (as mentioned above) be based on physical conditions of the radiation treatment system. The constraints on the positions can also be described by an arrangement planning volume, as will be described below.

The constraints on the positions of and/or positional changes in the treatment beam are also referred to here as constraints on the beam positions and/or constraints on the positional changes in beam position. In other words, positions of the (active or inactive) treatment beam are beam positions.

The determined control data can in particular be outputted by a computer as control signals for controlling the position of a treatment beam source, in particular so as to control the position of the origin of the treatment beam and the direction of the treatment beam. In this way, the treatment beam position is controlled. By changing the position of the treatment beam in accordance with the arrangements, the treatment beam will follow the determined arrangement.

Preferably, the step of providing the arrangement of beam positions involves determining at least some of the beam positions of the arrangement (preferably all) such that the treatment beam passes through the treatment body part. They are preferably determined on the basis of the treatment data which describe the position of the treatment body part in particular in a reference system. The reference system can be relative to the arrangement. Preferably, at least some of the determined beam positions lie in a different plane to other beam positions, particularly if this better fulfils the conditions described by the condition data than if all the beam positions lie in a common plane. In particular, at least some of the beam positions do not lie in a plane in which at least one of the other beam positions lies. In particular, at least one beam position of the arrangement does not lie in a plane defined by two other beam positions of the arrangement.

The condition regarding the radiation exposure in outside body parts is in particular a condition which sets a limit for the radiation exposure at a level which is lower than a limit described by the condition regarding the radiation exposure of the treatment body part. For instance, the condition regarding the radiation exposure in the outside body parts and the condition regarding the radiation exposure in the treatment body part is that the dose in the outside body parts is lower than a predetermined level or lower than a predefined percentage of the dose in the treatment body part. This percentage is in particular lower than 50% or 20% or 10% or 5% or 1% or 0.5% or 0.1%. In order to determine the dose, a maximum dose (or an average dose, for example the mean or median) in (the total or in regions of) the outside body parts and/or the treatment body part is in particular calculated. If an average dose is calculated in each of a plurality of outside body parts, the maximum of the average doses is in particular selected to represent the dose in the outside body parts. In accordance with one embodiment, the radiation exposure—in particular, a maximum dose in the outside body parts—is reduced and in particular minimised. In accordance with one embodiment, the condition regarding the radiation exposure in the outside body parts is that the radiation exposure is below a predetermined threshold value (in the total volume filled by the outside body parts or in at least 50% or 70% or 90% or 95% or 99% of said volume).

The condition regarding the radiation exposure in the treatment body part is in particular a condition which sets a limit for the minimum radiation exposure at a level which is higher than a limit described by the condition regarding the minimum radiation exposure in the outside body parts. In particular the condition regarding the radiation exposure in the treatment body part is a condition according to which the radiation exposure has to be above a predefined level (above the minimum radiation exposure), in particular within a predefined range. Given this condition, the radiation exposure in the outside body parts is in particular below the limit which describes the maximum radiation exposure, in particular minimized.

In accordance with an embodiment, the condition for the radiation exposure in particular outside body parts (also called special outside body parts) is below a predetermined level (threshold value).

In accordance with one embodiment, at least one specific so-called outside body part is identified. The condition data then preferably comprise outside body part data which describe the position (and/or geometry) of the specific outside body part or which describe a plurality of positions of a plurality of specific outside body parts. In particular, the radiation exposure conditions then include a condition regarding the radiation exposure, in particular in the outside body parts. In accordance with one embodiment, this condition is that the radiation exposure in the specific outside body part is lower than in other outside body parts and/or below a particular threshold value, wherein "lower than in other outside body parts" in particular means lower than the maximum value in the majority of the volume (in particular, in more than 50%, 70%, 90%, 95% or 99% of the volume) of the other outside body parts. In accordance with another embodiment, threshold values are assigned to the specific outside body parts which are in particular lower than the threshold value for other outside body parts (non-specific outside body parts), i.e. there is an assignment between the specific outside body parts and their respective threshold values. In accordance with another embodiment which can be combined with the previous embodiments, weighting factors are assigned to different outside body parts, in particular to the specific outside body parts. These weighting factors describe the importance of minimising the radiation exposure in the respective outside body parts. Thus, these weighting factors are taken into account when fulfilling a condition for minimising the radiation exposure in outside body parts, such that the radiation exposure is therefore smaller in some of the outside body parts (in particular, the specific outside body parts) than in other outside body parts. In accordance with another embodiment which can in particular be combined with the previous embodiments, the condition regarding the radiation exposure inside the treatment body part is that the radiation exposure is above a predetermined threshold value. This ensures that a sufficient dose for achieving the desired result of radiation therapy is reached in the treatment body part. In particular, the conditions regarding the radiation exposure described above can be combined.

In accordance with another embodiment, the degree to which the conditions (in particular, the radiation exposure conditions) described by the condition data are fulfilled is assessed. The conditions can be deemed to be fulfilled if at least one predefined condition (for instance Condition 1, 2, 3 or all of the radiation exposure conditions) is fulfilled. This can be achieved in a plurality of different ways. If, for example, different threshold values are set for the outside body parts and the treatment body parts, then the assessment is simply a binary decision, i.e. if the radiation exposure in the outside body part is below its respective threshold value and the radiation exposure in the treatment body part is above its respective threshold value, then the conditions are fulfilled, otherwise they are not fulfilled. The assessment can also involve a qualitative assessment of how well the conditions are fulfilled. A range of scores can for example be assigned to each of one or more outside body parts and the treatment body part. Depending on the radiation exposure in each of the parts (the outside body parts and the treatment body part), a score within said range of scores is determined. The different scores can be weighted and summed in order to determine a final score which qualitatively describes the degree to which the conditions (in particular, the radiation exposure conditions) are fulfilled. If, for example, the radiation exposure in the outside body parts is significantly below the threshold value assigned to said outside body parts, this translates into a high score. If the radiation exposure in the treatment body part is well above the threshold value, this likewise translates into a high score. The sum of all these individual scores then provides a qualitative indication of how well the conditions are fulfilled. In the given example, the conditions are fulfilled to a high qualitative degree if the sum of the scores is high. A qualitative threshold can then for example be defined, such that the conditions are only deemed to be fulfilled if the score is above the quality threshold. Alternatively, the arrangement which results in the highest score is for example selected from a plurality of candidate arrangements. As mentioned above, this more flexible condition can of course be combined with a rigid condition that the radiation exposure in the treatment body part is above a certain threshold value and/or that the radiation exposure in specific outside body parts is below a certain threshold value. In particular, the condition is deemed to not be fulfilled if one, two, three or more of the conditions described above is/are not fulfilled. New candidate arrangements are then for example calculated or received (e.g. as input from a user via a user interface) and/or a warning signal is outputted, as explained in more detail below.

As mentioned above, the step of assessing how well conditions are fulfilled can return a binary value (i.e. "condition fulfilled" or "condition not fulfilled") and/or an incremental or non-incremental (continuous) value which qualitatively describes how well conditions are fulfilled. Preferably, the step of providing the arrangement of beam positions comprises such a step of assessing. Thus, the step of providing the arrangement preferably comprises an assessing step which yields the results of the assessments, wherein the assessments in particular describe whether or how well the conditions are fulfilled by the different candidate arrangements. The assessment results can alternatively or additionally describe the radiation exposure in the outside body parts and/or the treatment body part. In particular, the assessment results can be given locally, for instance the different radiation exposure in the different body parts (outside body part, special outside body parts and/or treatment body part) can be indicated (for instance by using a map, in particular a color coded map). The method can then be constituted to wait for an input of a user which indicates if the assessment result is acceptable or not. If the input indicates acceptance, the proposed candidate arrangement is selected to be the determined candidate arrangement.

In addition to the assessing step, the step of determining the arrangement preferably also comprises a comparing step which compares the results of the assessments for the different candidate arrangements. In particular, it is possible that one of the candidate arrangements spans a plane surface. In particular this assessment of this candidate arrangement is compared with other candidate arrangements which in particular span a curved surface.

In particular, according to an advantageous embodiment, the candidate arrangement can be provided by being determined automatically. In particular, according to another advantageous embodiment, the candidate arrangements can be provided by being determined based on received user inputs. The user inputs can be received by a user interface (e.g. a keyboard or mouse). The user inputs can describe for instance one or more beam positions over a candidate arrangement. For instance, the input beam positions and/or the candidate arrangement determined based on the beam positions is checked whether the conditions described by the condition data are fulfilled. In particular, it is assessed whether the constraints on the position of the treatment beam and/or constraints on positional changes of the treatment beam are fulfilled. For instance there is a constraint that a beam source can perform a rotational movement having an angular velocity below a predefined level. Preferably, if the provision of the arrangement, in particular the determination of the arrangement is based on received user inputs (input data received from user), then the above described assessment step is performed. Preferably, the control data are only output by the data processing method or only determined by the data processing method based on a provided arrangement which fulfils the condition data. Preferably, the data processing method according to the present invention includes a step of outputting the control data. A particular constraint on the position of the treatment beam is that the treatment beam passes through the treatment body part. In particular a condition is that the treatment beam does not result in a radiation exposure in special outside body parts above a predefined level.

In particular, one of the different candidate arrangements can be selected automatically by the data processing method, in particular on the basis of the comparisons. In particular, the candidate arrangement which has the best assessment result, i.e. which best fulfils the conditions, is selected. In accordance with one embodiment, indication data are determined on the basis of the comparison and/or the assessment results. The indication data in particular describe the comparison and/or the assessment results. The assessment results can for example be ranked on the basis of the comparison, and the ranked assessment can be described by the indication data. Said indication data are preferably outputted using indication signals and/or in particular a user interface such as a screen or loudspeaker. In particular, the indication signals are audio signals and/or video signals and/or tactile signals. In accordance with this embodiment, a user can select one of the different candidate arrangements, on the basis of the indicated comparison result. The method according to the invention outputs the indication data and waits to receive selection data which describe the selected candidate arrangement which is to be the arrangement determined by the step of determining an arrangement of beam positions. In other words, the step of determining an arrangement of beam positions can thus be partly automated by outputting the indication data and receiving the selection data. The step of providing the arrangement of beam positions can also be fully automated. A plurality of candidate arrangements are then preferably provided automatically. The candidate arrangements are automatically assessed as to how well they fulfil the conditions—in particular, the results of the assessments are automatically compared, and one of the candidate arrangements is selected, in particular automatically or by a user, on the basis of the comparison.

The plurality of candidate arrangements can be provided in a variety of ways. In accordance with one option, a plurality of different candidate arrangements are stored in a database, and the database is accessed by the method in accordance with the present invention in order to acquire candidate data which describe the candidate arrangements. For automatically providing (for example, generating) candidate arrangements, the aforementioned conditions—including constraints on the positions of and/or positional changes in the treatment beam—are taken into account. Preferably, only the candidate arrangements which fulfil at least these constraints are therefore (automatically) provided to be assessed.

If a candidate arrangement already fulfils the constraints on the positions and/or positional changes, then the assessment is preferably based on the remaining conditions, in particular the conditions regarding the radiation exposure.

In accordance with one embodiment, the method in particular allows a user to freely determine an arrangement as a candidate arrangement and/or to determine at least some of the beam positions of a candidate arrangement, i.e. candidate beam positions (which are to be assessed), wherein the assessing step in particular also then assesses whether the candidate arrangement and/or candidate beam position fulfils the constraints on the positions of and/or positional changes in the treatment beam. The candidate arrangements are not then provided by a fully automatic determination but the providing step includes a step of receiving an input from a user by the data processing method.

In accordance with one embodiment, the candidate arrangements are determined on the basis of condition data which describe the constraints on the beam positions and/or positional changes in beam position and in particular describe an arrangement planning volume. The arrangement planning volume describes the volume within which arrangements of beam positions are possible. In accordance with a straightforward method, the possible beam positions within the arrangement planning volume are varied in discrete increments until all the possible candidate arrangements have been determined. This plurality of candidate arrangements then represents the candidate data which are used as the basis for assessing how well the conditions are fulfilled. For determining candidate arrangements, conditions which are described by the condition data are in particular taken into account, in particular the condition that a candidate arrangement is designed to span a surface which does not pass through specific outside body parts and/or the condition that all the beam lines end in the treatment body part. Another optional condition is that the beam positions of two beams passing through the treatment body part from opposite sides are inclined with respect to each other, such that the volume of outside body parts situated in the overlap of the volumes of the two beams is minimised. In accordance with one embodiment, it is thus even possible to take into account conditions, described in particular by the condition data, when determining candidate arrangements. Alternatively or additionally, the same or other conditions can be taken into account when determining the arrangement in the step of determining the arrangement, for example by selecting one of the candidate arrangements. The step of providing different candidate arrangements of beam positions can also be a step in which the different candidate arrangements are determined (for example, generated) by the method or in which the different candidate arrangements are received, for example from another data processing method or via an interface, in particular a user interface. Preferably, the different candidate arrangements of beam positions provided are such that the beam positions of at least one of the different candidate arrangements do not lie in a common plane.

Preferably, the step of assessing how well a condition is fulfilled is performed automatically by the data processing method. The assessment results can be compared by the user on the basis of indicated assessment results or automatically by the method, in particular the data processing method. Unless explicitly described otherwise, the steps described with respect to the data processing method are in particular automatically performed by the data processing method.

In accordance with one embodiment, the selecting step is automatically performed by a data processing method. In accordance with a partly automated method, the assessment result is indicated by the method, and selection data (which indicate a selection made by the user) are received by the method.

In accordance with the invention, candidate data are preferably provided which describe a candidate arrangement of beam positions. The data can be provided in different ways. The candidate data can for example be received (for example, via an interface and/or from a data memory). In accordance with another embodiment, candidate beam positions are received (for example, via a user interface). Candidate arrangements are determined on the basis of these candidate beam positions. The candidate beam positions can be incomplete, i.e. only partly describe an arrangement of beam positions, such that a plurality of arrangements which include the received candidate beam positions are possible. Nevertheless, the candidate beam positions represent corner stones for determining the candidate arrangements. In accordance with another embodiment, the candidate arrangements are determined by the method, as already described above. As also mentioned above, there are a number of different possible ways of determining the candidate arrangements.

Where, as mentioned above, candidate beam positions are received which do not completely describe an arrangement, the arrangement can be determined interactively, in particular in an interaction with the user, i.e. the user inputs a candidate beam position, and possible arrangements which include the inputted beam position are determined. The different possible candidate arrangements are then assessed, and the assessment result is outputted to the user. The user then selects another candidate beam position (i.e. selection data are received by the method) which is part of one of the proposed candidate arrangements. Candidate arrangements are then determined again, on the basis of the first and second candidate beam positions, and assessed. On the basis of this assessment, the user then proposes a third candidate beam position, and so on until a candidate arrangement has finally been determined by the received selection data. If the predetermined candidate arrangement is not a good candidate arrangement (i.e. the conditions are only fulfilled to a low qualitative degree), then it is possible in accordance with one embodiment for the user to propose another candidate beam position. In particular, indication data which preferably comprise a warning to the user are outputted if the proposed candidate beam position results in candidate arrangements which do not fulfil the conditions defined by the condition data.

In accordance with one embodiment, the radiation treatment system is designed to emit a treatment beam to the treatment body part from two opposite directions. The radiation treatment system is for example designed to continuously move the beam source from a first position to a second position, wherein the second position is opposite the first position, in particular the beam source is in a position in which the beam source can emit a treatment beam to the treatment body part from the first position in a direction which is opposite to the direction in which the beam source can emit a treatment beam from the second position. The (active or inactive) beam positions corresponding to the first and second positions overlap fully, although the beams can be emitted in opposite directions, i.e. the (beam) volume of the two beams at the two fully overlapping beam positions also overlap (n case of active beam position) or would overlap (in case of inactive beam position). The overlap of the volumes of the two beams is in particular not a full overlap, since the beams can have a conical shape, but the overlap would be a full overlap if the volumes had an identical cylindrical shape.

If the radiation treatment system is controlled as described previously, outside body parts which are subjected to the treatment beam when the beam source is in the first position are again subjected to the treatment beam when the beam source is in the second position. In accordance with the invention, subjecting outside body parts to the treatment beam twice in this way is preferably reduced or avoided, in order to reduce the volume in which two beams overlap. Since two beams act on the overlapping volume, there is a higher dose in this overlapping volume than in the volumes of outside body parts in which there is no overlap. In order to achieve this reduction, the condition data in accordance with the invention preferably define that overlapping beam positions assigned to beams of opposite emission directions are not allowed (at least for a part of the arrangement), and in particular that the beam positions have to be inclined with respect to each other (at least for a part of the arrangement).

Preferably, the condition regarding the radiation exposure in outside body parts is or includes the condition that if orthogonal projections of two different beam lines onto a so-called treatment plane are parallel and overlap each other if mirrored at the treatment body part, then the two beam lines are determined in such a way that they do not fully overlap in the outside body parts if extended beyond the treatment body part. This applies preferably at least for a part of the arrangement. The two different beam lines are preferably inclined with respect to each other. Preferably, at least two of the beam lines are inclined with respect to each other, while the orthogonal projections of the two beam lines (in particular, the two positions of the central lines of the treatment beams) would overlap on the treatment plane if extended beyond the treatment body part.

The treatment plane is preferably a plane which passes through the treatment body part. The treatment plane is preferably a plane within which the radiation treatment system can change the beam positions while the beam positions pass through the treatment body part. In particular, an axis which is normal to the treatment plane is a rotation axis about which a treatment beam source can be rotated around the treatment body part and which passes through the treatment body part. If the beam source rotates 180° about the axis from a first to a second position, the beam source preferably rotates simultaneously about a second axis which is perpendicular to the aforementioned first axis. In this way, the treatment beam passes through the treatment body part, if the beam source is in the first and second position, while the corresponding beam positions (corresponding to the first and second position of the beam source) are inclined with respect to each other.

The treatment plane can in particular be defined to be a plane which passes through the treatment body part. In particular, there are a plurality of planes within which the beam positions can lie and which pass through the treatment body part. In other words, the radiation treatment system is in particular constituted to move the beam source relative to the treatment body part (by moving the beam source and/or the couch) so that the beam source can move in a plurality of different planes. One of these planes can be selected as a treatment plane. In case there are for instance not just two rotational degrees of freedom but three rotational degrees of freedom for movement of the treatment beam source relative to the treatment body part, there can be a first and second treatment plane which are in particular perpendicular to each other.

A movement plane describes a plane within which the beam source is movable relative to the treatment body part. There is in particular a plurality of movement planes. Preferably, that one of the movement planes is defined to be the treatment plane which lies in the middle of the movement planes. The movement planes are in particular those movement planes which result if the movement performed within a movement plane is achievable by just two rotational degrees of freedom. In particular the treatment plane is that plane out of the movement planes within which most of the arrangement is lying. In particular, the treatment plane is that one of the movement planes which has the highest number of intersections between the arrangement and the movement plane. Preferably, there is at least one, in particular at least two or at least three intersections between the arrangement and the treatment plane. Also this represents preferably a constraint according to which it is allowed that the beam positions are not in a common plane. In particular, according to this constraint an intersection with the treatment plane is allowed.

As mentioned above, the arrangement is preferably determined in such a way that the beam positions of the arrangement span a (virtual) surface which is preferably at least partly curved. This means in particular that the plurality of (active or inactive) beam lines in the plurality of (active or inactive) beam positions span the surface. Preferably, the virtual surface intersects the above-mentioned treatment plane. The treatment plane is a plane which preferably passes through the treatment body part and within which the beam lines can, but need not, lie. The beam source is in particular designed to be able to move along a path (referred to as a "beam source path") which lies within the treatment plane and which is preferably bent around the treatment body part. However, the beam source path can also preferably leave the treatment plane. According to the condition data (positional constraints), the arrangement is preferably allowed to be determined, in particular forced to be determined in such a way that the spanned virtual surface defined by the arrangement (in other words, by the beam positions of the arrangement) does not lie fully within the treatment plane but is at least partly outside the treatment plane. The beam source path is preferably bent around the treatment body part, wherein "bending" means in particular that the path is a closed loop or that the path only partly surrounds the treatment body part. In particular, the condition data allow, and in particular define that the spanned virtual surface intersects the treatment plane at least once and preferably at least twice. If the path of the beam source is projected onto a circle around the treatment body part, the projected beam source path is preferably longer than a quarter revolution (i.e. more than 90°) or in particular longer than half-revolution (i.e. more than) 180° and in particular longer than a three-quarter revolution (i.e. more than 270°) and is in particular a complete revolution (i.e. 360°). In other words, the path of the beam source is wound around the treatment body part over more than 180°, in particular over more than 270°, or is in particular wound around the treatment body part over 360°.

The aforementioned surface is preferably curved, in particular undulated (in particular, wave-shaped). Preferably, all the treatment beams pass through the treatment body part. In particular, an imaginary line (referred to as the "surface line") which lies in the curved surface and has an equal distance from the treatment body part (and thus at least partly surrounds the treatment body part) crosses the treatment plane, moves away from the treatment plane and then approaches and intersects the treatment plane again. An example of a surface line is a line which connects the starting points of the beam lines and thus represents the path of the beam source. If a plurality of such surface lines have different distances from the treatment body part, then the distance between a point on the surface line and the treatment plane preferably increases as the distance between the surface lines and the treatment body part increases. The condition data preferably include conditions according to which the arrangement can be determined, in particular has to be determined in such a way that the surface spanned by the arrangement exhibits at least one of the properties of the spanned (virtual) surface mentioned here.

If the beam source is activated and a treatment is started, the beam source in particular continuously moves forward along the beam source path relative to the treatment body part by controlling the position of the beam source and/or the position of the couch. In particular, the beam source path is determined on the basis of the determined arrangement. The orthogonal projection of the positions of the beam source along the beam source path onto the treatment plane preferably shows a continuous forward movement around the treatment body part (in particular, without any backward movement) from a starting point of the beam source path to a finishing point of the beam source path; this also reduces the doses for outside body parts and increases the treatment speed. It is a preferred feature of the treatment plane that there is no back and forth movement of the projection along the projected path during a movement from the path starting point to the path finishing point and/or during a movement from the path finishing point to the path starting point. The position of the beam source is in particular represented by the starting point of the beam line assigned to the beam position of the beam emitted by the beam source. The starting point of the path of the beam source is called the path starting point, and the corresponding finishing point is called the path finishing point. The projection of the path starting point onto the treatment plane is called the projected path starting point, and the corresponding projection of the path finishing point is called the projection path finishing point. In accordance with one embodiment, the beam source performs a forward movement from the path starting point to the path finishing point. A backward movement is also possible. In accordance with one embodiment, the projection of this backward movement can partly or fully overlap with the projection of the forward movement. However, the beam source path of the forward movement preferably differs from the beam source path of the backward movement. This can lower the dose in outside body parts as compared to an identical beam source path for the forward and backward movement.

If the position of the treatment body part, in particular the central position of the treatment body part, is the centre of a circle which lies in the treatment plane, then the projected beam source path can be projected onto this circle. The projection of the projected path starting point and the projection of the projected path finishing point onto the circle represent the starting and finishing points of the angular range which is referred to as the treatment plane angular range. This treatment plane angular range can be 360° or less. The angular range is in particular greater than 90°, preferably greater than 180° or greater than 270°.

The beam source path can also be projected onto a plane which is perpendicular to the treatment plane and is referred to as the perpendicular plane. Preferably, the axis of the aforementioned circle lies in the perpendicular plane. This projected path (projected onto the perpendicular plane) is preferably not a straight line but rather a curved line (undulated line) from the projected starting point to the projected finishing point in said perpendicular plane.

In accordance with one embodiment, the condition data can—as mentioned above—include constraints on the geometry (size and/or shape) and/or position of the arrangement planning volume within which the determined arrangement of beam positions has to be confined. In other words, all arrangements allowed to be determined according to the constraints on the geometry and/or position of the arrangement planning region are (fully) within the arrangement planning region. The term "geometry" as used here encompasses the meaning of "size and/or shape". The position and/or geometry of the arrangement planning volume is in particular constrained by mechanical constraints of the radiation treatment system, in particular the beam source driving device. In particular, the position of the patient couch can block the free movement of the beam source (when driven by the beam source driving device) and can thus constrain the geometry and/or possible positions of the arrangement planning volume. If, for example, the support structure of the treatment beam source is ring-shaped and the couch penetrates the ring, then a rotation of the ring about a (virtual) axis (for example, the X-axis in FIG. 1) which intersects the ring twice (at opposite points of the ring) and in particular lies in the treatment plane and is in particular perpendicular to the axis of the ring is restricted by the couch, and a complete rotation about this (virtual) axis is not possible. In particular, the possible finishing points of the rotation of the ring about the axis is defined by the positions at which the ring abuts against the couch. The beam source driving device can also be designed such that the beam source can only be rotated about a limited number of axes, for example two or three axes, and in particular in two or three rotational degrees of freedom. At least one of these rotations can have an angular range which is smaller than 360°. Translational movements of the beam source, as performed by the beam source driving device, can also be restricted to a limited number of directions (for example, 1 or 2 or 3), in particular a limited number of translational degrees of freedom and/or can be respectively restricted to a limited range.

If the beam source is attached to a robot arm, then there can also be restrictions due to the couch or due to the mechanical properties of the robot arm. The above examples of restrictions can result in constraints on the geometry and/or position of the arrangement planning volume. These constraints are preferably expressed in the condition data.

In accordance with one embodiment, the condition data comprise the constraints on the geometry and/or position of the arrangement planning volume, as mentioned above. These constraints are then preferably taken into account when determining the arrangement of beam positions.

The radiation treatment system can also be designed to change the shape of the treatment beam, for instance by using an MLC (multi-leaf collimator). The shape of the treatment beam is preferably taken into account when assessing how well the conditions are fulfilled, in particular the condition regarding the radiation exposure in outside body parts and the condition regarding the radiation exposure in treatment body parts. In accordance with one embodiment, an optimum shape for the treatment beam is in particular automatically determined in accordance with the beam position, such that the conditions described by the condition data are optimally fulfilled. The optimum shape can be automatically determined by assessing the qualitative degree to which the condition is fulfilled for a plurality of candidate beam shapes in the respective beam positions of candidate arrangements. In particular, the radiation exposure in outside body parts and/or treatment body parts is calculated for different candidate beam shapes, and the calculation result is used as a basis for the assessment. When determining the shape of the treatment beam, the aforementioned constraints on the shape of the treatment beam (in particular constraints on changes in the shape of the treatment beam) are in particular taken into account. Preferably, those ones of the plurality of candidate beam shapes are selected for the respective beam positions which are assessed to best fulfil the conditions.

As mentioned above, the treatment radiation system is preferably designed such that the treatment beam source can (but need not) be moved (relative to the treatment body part), in order to emit treatment beams which exhibit beam positions which lie in a plane and cover a range of different directions of the emitted beam relative to the treatment body part. A plurality of such planes (movement planes) can be provided.

Data are also preferably provided which describe the possible range of speeds of changes in the treatment beam positions as the treatment beam follows the arrangement in accordance with the control data. This range of possible speeds is preferably described as a constraint by the condition data. The speed of changes (e.g. translational or rotational changes) in the treatment beam positions influences the dose applied to the outside body parts and the treatment body part. In accordance with one embodiment, the speed of changes in treatment beam positions is increased if the treatment beam passes through specific outside body parts or outside body parts within which the radiation exposure should be lower than in other outside body parts. Thus, in accordance with another embodiment, the method according to the invention determines not only the arrangement but also the speed of positional changes. The control data preferably include data for controlling the speed of changes in the treatment beam positions and/or control data for controlling the shape of the treatment beam. In particular, the radiation exposure in the outside body part and/or treatment body part is determined for different candidate speeds in the respective candidate beam positions. The speeds for different beam positions which best fulfil the radiation exposure conditions (and still fulfil the conditions regarding positional changes as mentioned above) are in particular selected on the basis of the determination results. The selected candidate speeds can differ for different beam positions. The condition data can further define constraints for change of speed, in particular an allowed range of acceleration, in particular an upper limit of acceleration. The term "radiation exposure conditions" covers at least one of the conditions regarding a radiation exposure described in this document.

In accordance with another embodiment, the condition data include constraints on the dose rate of the treatment beam, i.e. the radiation treatment system is designed to emit treatment beams which deliver dose rates which are within a predetermined range. Alternatively or additionally, the constraints on the dose rate can be determined by a user, in view of the treatment body part and/or outside body part which is subjected to the treatment beam. The constraint on the dose rate is preferably used to determine the arrangement of the beam positions and/or the speed of changes in the treatment beam and/or the shape of the treatment beam. In particular, the control data include data for controlling the dose rate of the treatment beam.

Couch volume data are preferably also provided which describe the relationship between the positions of the couch and the geometry and/or position of the arrangement planning volume. The couch is designed to allow a patient to be placed on it. As mentioned above, the couch can influence the geometry and/or position of the arrangement planning volume. If the position of the couch is changed, the geometry and/or position of the arrangement planning volume can change in accordance with the couch position. This interrelationship between the couch position and the geometry and/or position of the arrangement planning volume is preferably described by the couch volume data. Preferably, an optimization algorithm is used in order to determine an optimum couch position or a plurality of optimum couch positions (in particular a discrete or continuous sequence of couch positions) which result in an optimum arrangement. In particular, the control of the beam positions in accordance with the arrangement can result in a change of couch positions during treatment. Preferably, this is considered when determining a plurality, in particular a (continuous or discrete) sequence of optimum couch positions which sequence describes a change of the couch positions during treatment. A discrete sequence describes a plurality of positions of the couch which are adopted one after the other. At least at some of the adopted positions, the couch is motionless for some time (e.g. for at least 1 s or 10 s). A continuous sequence describes a multiplicity of positions (between the start and end position) which passes during a continuous movement of the couch. In accordance with one embodiment of the present invention, the above-mentioned constraints on the geometry and/or position of the arrangement planning volume are preferably determined on the basis of a planned position of the couch. The planned position of the couch is preferably described by couch data which can be received or determined. In accordance with one embodiment, the couch data represent planned candidate positions which are varied in order to vary the constraints on the geometry and/or position of the arrangement planning volume due to the relationship between the couch positions and the geometry and/or position of the arrangement planning volume. In accordance with one embodiment, a plurality of candidate arrangements are determined for a plurality of planned candidate couch positions. In accordance with this embodiment, the candidate couch position which best fulfils the radiation exposure conditions is preferably selected. In other words, candidate arrangement planning volumes are determined on the basis of candidate couch positions described by the couch data, which in this respect can also be referred to as "candidate couch data". The candidate couch data provided can be stored in a data memory and retrieved by a data processing method or can be determined by the data processing method by varying the different possible couch positions, to give but a few examples of how candidate couch data can be provided. If a plurality of candidate arrangement planning volumes have been determined, then the optimum arrangement of beam positions is preferably determined (respectively) for each of said determined candidate arrangement planning volumes. The respective optimum arrangements are preferably determined as described above by means of an assessment step which assesses how well the conditions described by the condition data, in particular the radiation exposure conditions, are fulfilled. The best of the optimum arrangements is then preferably selected from the plurality of optimum arrangements in a following step. A particular couch position (and a particular arrangement planning volume) or a sequence of particular couch positions is then assigned to this best optimum arrangement. Thus, this selection procedure can also be used to determine the couch position. In particular, control data for controlling the position of the couch are determined which control the position of the couch so as to correspond to the determined couch position.

In accordance with one embodiment of the radiation treatment system, the beam source driving device is designed to move about at least two axes, i.e. a first axis and second axis. The radiation treatment system is preferably designed such that a simultaneous movement about the first axis and second axis is possible. In accordance with this embodiment, the condition data preferably describe the constraints on the positions of and positional changes in the treatment beam, in particular the constraints on the arrangement planning volume, by means of a first angular range of allowed first rotational angles about the first axis and/or a second angular range of allowed second rotational angles about the second axis. Preferably, both axes are virtual axes. During treatment, both axes preferably pass through the treatment body part. In other words, the treatment body part is preferably arranged such that both axes pass through the treatment body part. The above-mentioned treatment plane is preferably selected to be perpendicular to the axis which is assigned the larger angular range of allowed rotational angles. In accordance with another embodiment, there are not only two axes about which the beam source can be rotated or moved but rather also at least a third axis which is perpendicular to the other two axes. Accordingly, a third angular range of allowed third rotational angles about the third axis is preferably also defined, wherein the treatment body part is then preferably arranged such that the third axis also passes through the treatment body part. In accordance with one embodiment, couch control data are preferably determined on the basis of the positions of the first and/or second and/or third axis and the relative position between the treatment body part and the couch, such that the axes pass through the treatment body part. During the movement of the beam source about the first and/or second and/or third axis, the distance between the beam source and the axis can be constant or variable (e.g. due to a movement of the couch and/or the beam source relative to the upper structure).

The method in accordance with the invention is in particular a data processing method. The data processing method is preferably performed using technical means, in particular a computer. The computer in particular comprises a processor and a memory in order to process the data, in particular electronically. The calculating steps described are in particular performed by the computer. Determining or calculating steps are in particular steps of determining data within the framework of the technical data processing method, in particular within the framework of a program. A computer is in particular any kind of data processing device and can be a device which is generally thought of as such, for example desktop PCs or notebooks or netbooks, etc., but can also be any programmable apparatus, such as a mobile phone or an embedded processor. A computer can in particular comprise a system (network) of "sub-computers", wherein each sub-computer represents a computer in its own right. A computer in particular comprises interfaces in order to receive data and/or to perform an analogue-to-digital conversion.

Where data are "provided", this means that they are ready for use by the method or program in accordance with the invention. The data can achieve this state of being "provided" or "ready for use" by for example being generated, in particular detected or captured (for example by analysis apparatus—for example, x-ray apparatus—for determining the position of the treatment body part and/or specific outside body parts) or by being inputted (for example via interfaces). The data can also achieve the state of being provided by being stored in a data memory (for example a ROM, RAM, CD and/or hard disc) and thus ready for use within the framework of the method or program in accordance with the invention. The expression "providing data" (within the framework of a data processing method) in particular encompasses the scenario in which the data are determined by the data processing method or program. The meaning of "providing data" also in particular encompasses the scenario in which the data are received by the data processing method or program, in particular in order for the data to be further processed by the data processing method or program. The expression "providing data" can therefore also for instance mean waiting to receive data and then receiving the data. The received data can for instance be inputted via the interface. "Providing data" can also mean that the data processing method or program performs steps in order to (actively) acquire the data from a data source, for instance a data memory (for instance, a ROM, RAM, database, hard disc, etc.), or via the interface (for instance, from another computer or a network).

Within the framework of the invention, computer program elements can be embodied by hardware and/or software (this also includes firmware, resident software, micro-code, etc.). Within the framework of the invention, computer program elements can take the form of a computer program product which can be embodied by a computer-usable or computer-readable storage medium comprising computer-usable or computer-readable program instructions, "code" or a "computer program" embodied in said medium for use on or in connection with the instruction-executing system. Such a system can be a computer; a computer can be a data processing device comprising means for executing the computer program elements and/or the program in accordance with the invention. Within the framework of this invention, a computer-usable or computer-readable medium can be any medium which can include, store, communicate, propagate or transport the program for use on or in connection with the instruction-executing system, apparatus or device. The computer-usable or computer-readable medium can for example be, but is not limited to, an electronic, magnetic, optical, electromagnetic, infrared or semiconductor system, apparatus or device or a medium of propagation such as for example the Internet. The computer-usable or computer-readable medium could even for example be paper or another suitable medium onto which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments. The computer and/or data processing device can in particular include an indication information device which includes means for outputting indication information. The indication information (for example, a warning) can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The program in accordance with the invention causes the computer to perform one of the methods described in this document, which are in particular data processing methods, when it is running on said computer or loaded onto said computer. The present invention is also directed to a program storage medium on which the program is stored (in particular in a non-transitory state) such as a CD or DVD or ROM or hard disc, etc. The invention is also directed to a computer on which the program is running or into the memory of which the program is loaded. An example of a memory is any kind of data source such as a hard disc or ROM or RAM, etc. The present invention is also directed to a signal wave which carries information, in particular in the form of data, which represents the program. The program in particular comprises code which is adapted to perform the steps (in particular all the steps) of at least one of the methods, in particular the data processing methods described in this document. The program in particular performs all the steps of the respective methods.

The present invention is also directed to a method which comprises the data processing method as described above and which receives signals (for example from an analysis apparatus) and/or outputs signals. Signals are of course technical in nature. In particular, the method outputs control signals, based on the determined control data, in order to control the beam position of the radiation treatment system. The control signals in particular control the position of the beam source. To this end, the control signals preferably control a beam source driving device or driver which is designed to change the position of the beam source. Thus, the method preferably comprises a step of controlling the beam positions using a beam source driver which is controlled by the control signals outputted in accordance with the method.

The invention is also preferably directed to a radiation treatment system which comprises the above-mentioned computer for determining the control data and for outputting control signals corresponding to the control data. The system also preferably comprises a couch for supporting the patient. The radiation treatment system also preferably comprises a beam source driver which can comprise a support structure for (mechanically) supporting the treatment beam source. In particular, the support structure supports the treatment beam source as it is moved. As mentioned above, the mechanical parts of the radiation treatment system such as the couch or the beam source driver can in particular lead to constraints on the arrangement planning volume. In particular, the beam source driver allows and is able to cause the movement of the radiation beam source relative to the couch, within the bounds of said constraints. The beam source driver is preferably adapted to receive the control signals from the computer in order to change the position of the beam source in accordance with the control signals received from the computer (in particular relative to the support structure). In particular, there is also a couch driver which moves the couch relative to the support structure. The position of the beam source and/or of the couch is thus controlled so that the beam positions follow the determined arrangement of beam positions during treatment.

The beam source driver preferably comprises at least two independent sub-drivers for independently moving the beam source in different degrees of freedom. The control data preferably comprise at least two sets of sub-control data for controlling the at least two sub-drivers which can comprise independent moving mechanisms for independently changing the position of the beam source (relative to the couch, in particular relative to the treatment body parts). The control data optionally comprise another set of control data for controlling the couch driver to change the position of the couch (discretely or continuously) during treatment (i.e. when the beam position continuously follow the arrangement and when the treatment beam is at least intermittently emitted).

One example of independently moving mechanisms is represented by motors which can be controlled independently, wherein each of the moving mechanisms (motors) is in particular capable of changing the position of the beam source in a different (rotational and/or translational) degree of freedom. Each moving mechanism is in particular capable of moving the beam source in a plane which differs from the plane in which the other moving mechanism is capable of changing the position of the beam source. Each of the at least two independently moving mechanisms is in particular responsible for an independent roll, yaw or pitch movement about respective virtual axis or a translational movement. Although the movements are independent, the control data are preferably designed to allow for simultaneous movement. The control data are in particular constituted so they can be designed to control the beam positions so that at least two of the sub-drivers (or at least one sub driver and the couch driver) are controlled so as to cause a movement of the beam source.

Preferably, at least some of the control data are determined in such a way that first and second sub-control data are designed to control the movement of a first and second moving mechanism and to control the treatment beam so as to be active while the sub-drivers are controlled such that they move the beam source. The method in accordance with the invention in particular causes a computer to output (at least) first and second sub-control signals which correspond to the (at least) first and second sub-control data, in order to control the (at least) first and second sub-drivers during the treatment. In particular, the control signal causes the treatment beam to be emitted while the (at least) first and second sub-drivers are controlled by the control signal such that they move the treatment beam source. The control signal in particular comprises (at least) a first and second rotation control signal in order to independently cause a rotation about (at least) a first and second (virtual) axis by means of the (at least) first and second sub-driver (rotation mechanism), respectively. The (at least) first and second axes are in particular perpendicular to each other, such that at least two of the three movements (pitch, yaw and roll) about at least two of the axes are performed simultaneously, at least for a portion of the total movement of the beam source during the treatment.

In the following detailed description, additional features of the invention will be disclosed. Features of different embodiments can in particular be combined.

FIG. 4a shows a cross-section through treatment beams.

FIG. 4b shows a cross-section through treatment beams as viewed in the direction A shown in FIG. 4a, if the treatment beams in FIG. 4a have a planar arrangement.

FIG. 4c shows a cross-section through treatment beams as viewed in the direction A shown in FIG. 4a, if the treatment beams in accordance with an embodiment of the invention have a non-planar arrangement.

Figure 1:
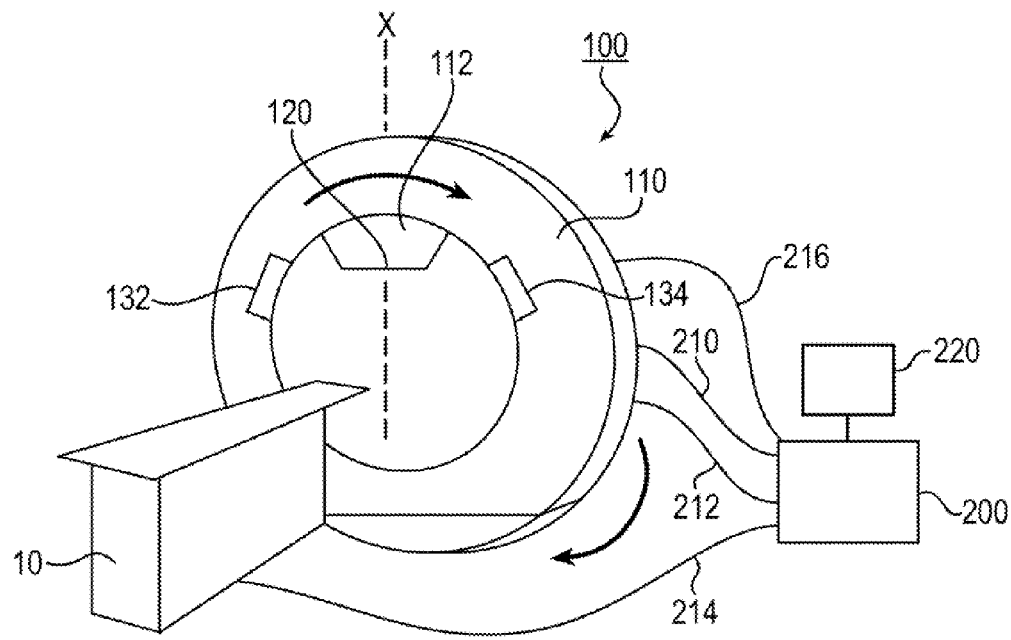
FIG. 1 shows a radiation treatment system in accordance with the invention.

FIG. 1 shows an embodiment of a radiation treatment system in accordance with the invention. A radiation treatment device 100 in accordance with one embodiment of the invention comprises a beam source driver which comprises a support structure 110 for supporting a beam source 120.

The support structure 110 can exhibit the ring-shaped structure shown in FIG. 1. The support structure 110 can be moved in at least two degrees of freedom—in the example shown, in two rotational degrees of freedom. One of these two movements can be a rotation about a first axis X which is shown by a dashed line in FIG. 1 and which is in particular a midline of the ring-shaped structure which in particular divides the ring into two equal parts (and thus intersects the ring twice). The dashed line represents a rotational axis about which the support structure 110 can be rotated. The rotational axis in particular passes through the central position of an opening through which the treatment beam is emitted from the beam source 120 when the beam source is in its base position. The base position is in particular the starting position for the largest possible maximum positional changes in each possible direction of positional changes in the beam source. The position of the beam source is preferably controlled by a beam source driver 110, 112 which allows the position of the treatment beam emitted by the beam source to be changed. The beam source driver in particular comprises another support structure which is in particular a gimbal 112. The beam source 120 can preferably also be rotated about a second axis which is perpendicular to the first axis X and which preferably passes through the centre of the ring-like support structure 110. This rotation about the second axis preferably corresponds to a movement in a second (rotational) degree of freedom. Preferably, the two movements (rotations) can be controlled independently.

In the embodiment shown, two analysis apparatus (monitoring devices) 132 and 134 are provided in order to determine (in particular, monitor) the position of the treatment body part.

This in particular allows the treatment beam to be directed in such a way that it passes through the treatment body part even if the treatment body part is moving, due for example to vital functions of the body. In particular, the beam source driver 110, 112 comprises (electric) motors in order to move the beam source in the at least two degrees of freedom. An electric motor is for example provided which rotates the beam source 120 about the second axis, for instance by moving the beam source along the inner surface of the ring-like support structure 110. At least one other (electric) motor is for example provided for rotating the (ring-like) structure 110 about the first rotational axis X. In accordance with one embodiment, the at least two motors are independently controlled by two independent sub-control signals. The independent sub-control signals can be provided via two signal lines 210 and 212 which connect the two motors respectively to a computer 200. The computer 200 can comprise a screen 220 and user interfaces such as a keyboard or mouse (not shown). Preferably, the2 program mentioned above is running on the computer 200 and/or stored on the computer 200. If the signal line 212 controls the rotation about the axis X, then in accordance with one embodiment, another signal line 216 controls the position of the other support structure 112 (in particular, the gimbal 112). This in particular enables the movement due to vital functions to be compensated. To this end, another motor (for example, a third motor) is preferably also provided.

In accordance with one embodiment, a signal line 214 connects the computer 200 to the patient couch 10. The signals transmitted via the signal line 210 are preferably used to control the position of the couch 10 (in particular, the upper surface of the couch on which the patient is lying or can be laid) relative to the radiation treatment device 100.

Figure 2:
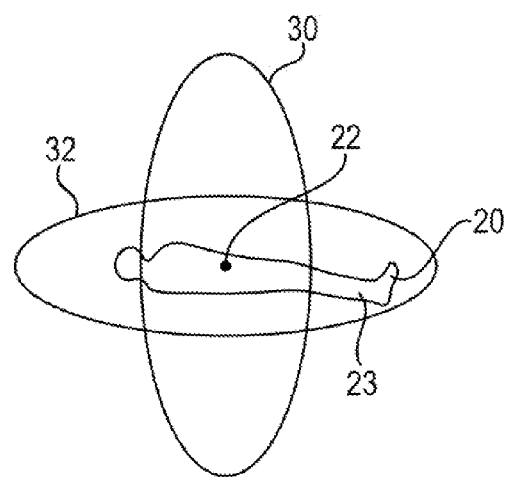
FIG. 2 shows two circles along which the radiation beam source can be rotated independently.

FIG. 2 shows a perspective view of two circles which describe degrees of freedom in which the beam source 120 can be moved around a treatment body part 22 of a patient 20. The treatment body part 22 is preferably at the centre of the two circles 30 and 32. Since the two movements of the beam source along the circles 30 and 32 can be combined, it is possible not only to move the beam source 120 in one plane in which the circle 30 lies or in one plane in which the circle 32 lies but also to position the beam source 120 outside the aforementioned two planes. The circle 30 represents a roll movement about the second axis from FIG. 1 (the Y-axis). The circle 32 represents a yaw movement about the first axis (the X-axis) from FIG. 1. In accordance with another embodiment, the radiation treatment device 100 is designed to be rotated about a third axis (the Z-axis, not shown) which is perpendicular to the first axis (X-axis) and the second axis (Y-axis, not shown). A pitch movement of the radiation treatment device 100—in particular, the beam source 120—is then also possible. To this end, the ring-like structure for example comprises a mechanical base which can be rotated at least partly about the Z-axis.

Since the motors for generating the rotational movement about the first and second axes can be controlled independently, beam positions can be chosen which are not all in a common plane. In particular, a multitude of different directions of the treatment beam (represented by beam positions) can be chosen in order that the treatment beam avoids passing through specific body parts (which are not to be hit by the treatment beam) but nevertheless passes through the treatment body part. In particular, the beam source 120 can continuously emit a treatment beam while following the arrangement of beam positions as determined by the computer 200. This applies even if the determined arrangement is a non-planar arrangement which has been chosen in order to minimise the dose in healthy body parts.

Figure 3A:
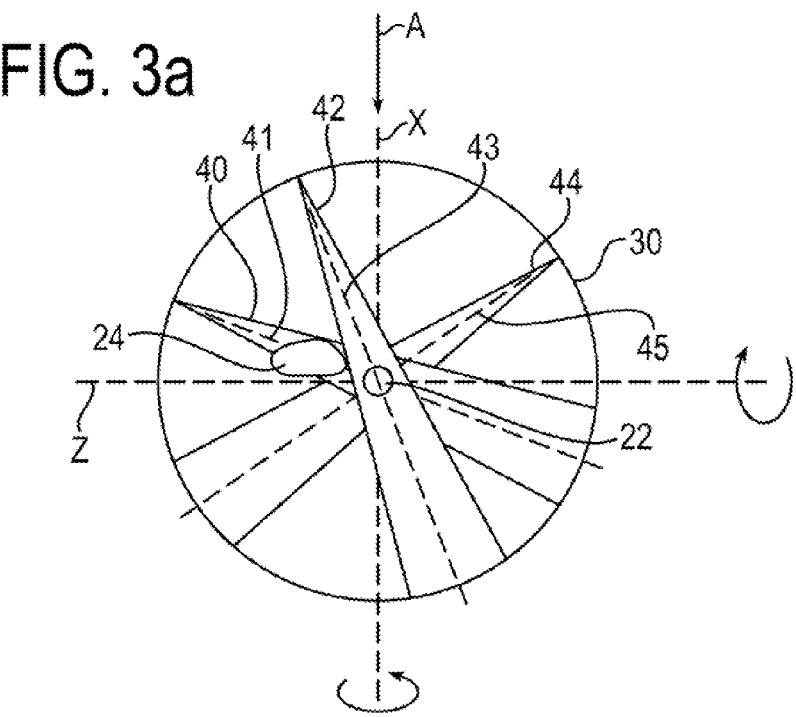
FIG. 3a shows a cross-section through treatment beams, treatment body parts and their specific outside parts.

How specific body parts can be excluded from receiving the treatment beam is explained with respect to FIG. 3. FIG. 3a shows the circle 30 and three examples of treatment beams 40, 42 and 44. These treatment beams each exhibit a conical shape and a central line 41, 43 and 45, respectively. All three treatment beams pass through the treatment body part 22 at the centre of the circle 30. The treatment beams between the treatment beams 40, 42 and 44 are not shown. In accordance with one embodiment of the invention, the treatment beam is moved continuously such that at a particular point in time, the treatment beam has the position of the treatment beam 40, and at a later point in time, the treatment beam has the position of the treatment beam 42, and at an even later point in time, the treatment beam has the position of the treatment beam 44. If the treatment beam performs a movement within a plane, i.e. in the plane 30, then the treatment beam would also hit a specific body part 24 which lies in the plane of the circle 30. However, it is possible in accordance with the invention for the treatment beam source to rotate not only about an axis Y which passes through the centre of the circle 30 and which is perpendicular to the axis X (the dashed line in FIG. 3a which extends from top to bottom and passes through the centre of the circle 30) but also about the axis X and to perform a yaw movement.

Figure 3B:
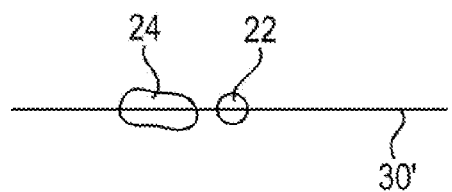
FIG. 3b shows a projected path of the treatment beam source in accordance with the prior art.

FIG. 3b shows the situation as viewed in the direction of the arrow A shown in FIG. 3a, i.e. along the axis X. FIG. 3b shows the scenario in which the beam source only moves within the plane of the circle 30. The straight line from left to right is a projection of the circle 30 into the plane which is perpendicular to the axis X. This straight line has the reference sign 30' and passes through the specific body part 24 and through the treatment body part 22. This indicates that the treatment beam passes through both the specific body part 24 and the treatment body part 22 as the beam source is moved along the circle 30.

Figure 3C:
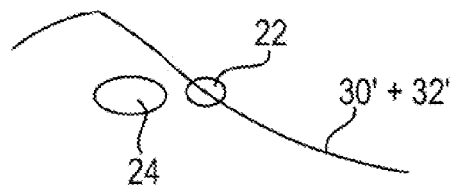
FIG. 3c shows a projected beam source path in accordance with the invention.

Since the beam source can perform not only a roll movement about the Y-axis but also a yaw movement about the X-axis, it is possible to determine an arrangement of beam positions which do not pass through the specific body part in any of the possible beam positions while the beam source is moved (from a starting position to a finishing position), but in which in particular all the beam positions pass through the treatment body part 22. How this is accomplished is shown in FIG. 3c. FIG. 3c is also a view in the direction A shown in FIG. 3a. The solid line is indicated as 30'+32' and describes a projection of the beam source movement onto the plane which is perpendicular to the X-axis. This beam source movement is performed by a combined rotation about the X-axis and the Y-axis. In other words, the line 30'+32' represents a projection of the multiplicity of origins of beam positions onto a plane which is perpendicular to the X-axis. These origins of the beam positions bypass the specific body part 24. Thus, the cone-shaped treatment beam does not pass through the specific body part but does pass through the treatment body part 22. This is achieved by causing the beam source to perform a yaw movement which deflects the beam positions out of the plane of the circle 30, such that the beam positions still pass through the treatment body part 22 (since the axis of the yaw rotation passes through the treatment body part 22) but bypass the specific body part 24. In other words, the multiplicity of beam positions describes a curved surface which exhibits a recess, in which the specific body part is embedded, but does not pass through the specific body part as the curved surface passes through the (centre of the) treatment body part.

FIG. 4a shows another preferred feature of the arrangement of beam positions. FIG. 4a shows the scenario in which two treatment beams 46 and 48 are opposite to each other, such that the central line (beam line) of the treatment beams 46 and 48 is identical. The central line is marked by the reference signs 47 and 49, respectively. The central line represents the beam position of the treatment beams 46 and 48. If the beam positions 47 and 49 are in the same plane, i.e. in the plane of the circle 30, then the situation shown in FIG. 4b arises. FIG. 4b is a view from the direction A (i.e. along the axis X) onto a plane which is perpendicular to the axis X and passes through the treatment body part. As can be seen, the treatment beams 46 and 48 cover a common region 52 (shown as a hatched region). This region 52 represents the overlapping volume of the two opposite treatment beams. The common region 52 is not simultaneously covered by the two beams, since the treatment beam is first situated at the position of the beam 46 and only later situated at the position of the beam 48. Nevertheless, the dose of both beams 46 and 48 does act on the region 52.

FIG. 4c shows the positions of the treatment beams 46 and 48 from FIG. 4a in a view from the direction A in accordance with an embodiment of the invention. The beam positions 47 and 49 do not overlap because the beam source has performed a rotational movement about the X-axis, while emitting the treatment beam, from the position of the beam 48 to the position of the beam 46. The result of this movement of the treatment beam about the X-axis while treating the treatment body part is that the overlapping region 52' (the hatched region) shown in FIG. 4c is smaller than the overlapping region 52 in FIG. 4b. The overlapping volume is therefore smaller and the volume of the region which is subjected to a higher dose than other outside body parts has thus been decreased. Thus, although the treatment beams 46 and 48 are opposite to each other when viewed as shown in FIG. 4a, i.e. from the Y-axis, the overlapping region 52' of FIG. 4c is smaller than the overlapping region 52 of FIG. 4b because the beam positions 47 and 49 do not overlap and are not in a common plane. This enables the volume of outside body parts subjected to the treatment beam twice to be lowered as compared to the scenario in which the beam positions are in the same plane and the treatment beams are opposite to each other, i.e. when the treatment beam performs a 180° rotation about the Y-axis.

Figure 5:
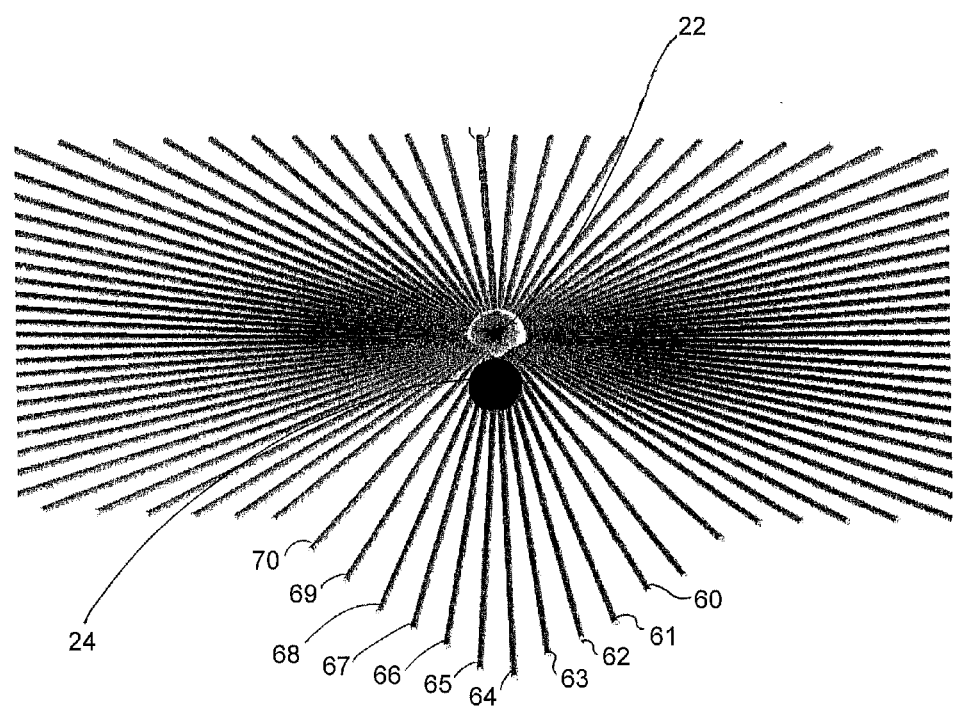
FIG. 5 shows a perspective view of a treatment beam arrangement in accordance with the invention which passes through a tumour but bypasses a specific body part.

FIG. 5 shows a perspective view of an arrangement of beam positions in accordance with the invention. Some of the individual beams are indicated by the reference signs 60 to 70. As can be seen, all the beams pass through the treatment body part 22. The beam positions 60 to 70 are not in a common plane but rather follow a curved or wave-like surface. Due to this curvature of the surface, the beams 60 to 70 do not pass through the specific body part 24 but rather pass around it. In the example shown in FIG. 5, the beams 60 to 70 pass behind the specific body part 24. However, all the treatment beams pass through the treatment body part 22. The beam source changes its position in accordance with the control signals from the computer 200, such that the treatment beam continuously follows the arrangement of beam positions as determined by the program, i.e. follows the curved surface determined by the arrangement of beam positions. The beam source can start the treatment, i.e. start emitting the treatment beam, at any possible position, for instance at the position of the beam 68, and then move for instance in a clockwise direction (as shown in FIG. 5), such that it ends at a finishing position which can for instance be the position of the beam 67.

Thus, the control data (and the corresponding control signals) preferably cause one of the driving mechanisms (for example, a motor) of the beam source to perform a continuous forward movement (in the clockwise or anticlockwise direction) in one degree of freedom from a starting point to a finishing point (which can be identical in the case of a circular movement). During this continuous movement from a starting point to a finishing point, at least some of the control data (and the corresponding control signals) cause a driving mechanism to move the beam source in another degree of freedom, i.e. to change its position in another degree of freedom. This movement (positional change) is performed at least partly during the movement from the starting point to the finishing point and can be a movement in one direction only or can in particular be a forward and backward movement. The movement can result in an undulated (for instance, wave-like) movement path of the beam source from the starting point to the finishing point.

Examples for radiation exposure conditions are for instance in case the prostate is the treatment body part that the minimum radiation dose is 70 Gy. Furthermore, a special outside body part would be the seminal glands. The maximum radiation dose (upper limit) for this special outside body part would be 50 Gy. Another possible condition for a special outside body part would be in case of the rectum that a maximum of 25-30% vol. is allowed to receive more than 75.6 Gy. That is, the radiation exposure conditions can also include conditions with respect to the volume as described above. In case a brain tumor is the treatment body part, the radiation exposure to for example the brainstem should not exceed approximately 50 Gy.

The aforementioned regions 52 and 52' are merely examples of outside body parts. In particular, any part 23 of the body 20 which is outside the treatment body part 22 is an outside body part.

The arrangement of beam positions shown in FIG. 5 can be determined by an optimization algorithm. Principles of the optimization algorithms are for instance described in "global optimization algorithms—theory and application—of Thomas Weise published in the internet under the URL: http://www.it-weise.de. Examples for optimization algorithms which can be employed in the present case are: Gradient based optimization algorithm, simulated annealing optimization algorithm, Dynamically Penalized Likelihood Algorithm. In these optimization algorithm the treatment data and the condition data are input as a constraint so that preferably the arrangement passes through the treatment body part and fulfils the constraints while the fulfillment of the radiation exposure conditions is optimized and while a curved arrangement is allowed.

The arrangement shown in FIG. 5 can also be a candidate arrangement, and a multitude of other candidate arrangements can be received or determined by the program. The candidate arrangement which best fulfils the conditions is then preferably selected. In particular, the candidate arrangement for which the radiation exposure in the treatment body part 22 is above a first threshold level and the radiation exposure in outside parts (except for the specific body part 24) is below a second threshold value (which is lower than the first threshold level) and the radiation exposure in the specific body part 24 is below a third threshold value (which is lower than the second threshold value) is selected or a corresponding arrangement is determined by the optimizer. Thus, data describing radiation exposure (e.g. the dose and/or energy and/or dose rate) of the treatment beam and in particular the shape and/or speed of the treatment beam source along a path defined by the arrangement of beam positions are preferably used to calculate the expected radiation exposure in the treatment body part and outside body parts and in particular in one or more specific body parts. According to an embodiment, the calculated radiation exposure is indicated to the user for different body parts so he can confirm the determined arrangement or select one of the candidate arrangements. According to another embodiment, one of the candidate arrangements is then automatically selected, as described above, on the basis of the calculation.

Figure 6:
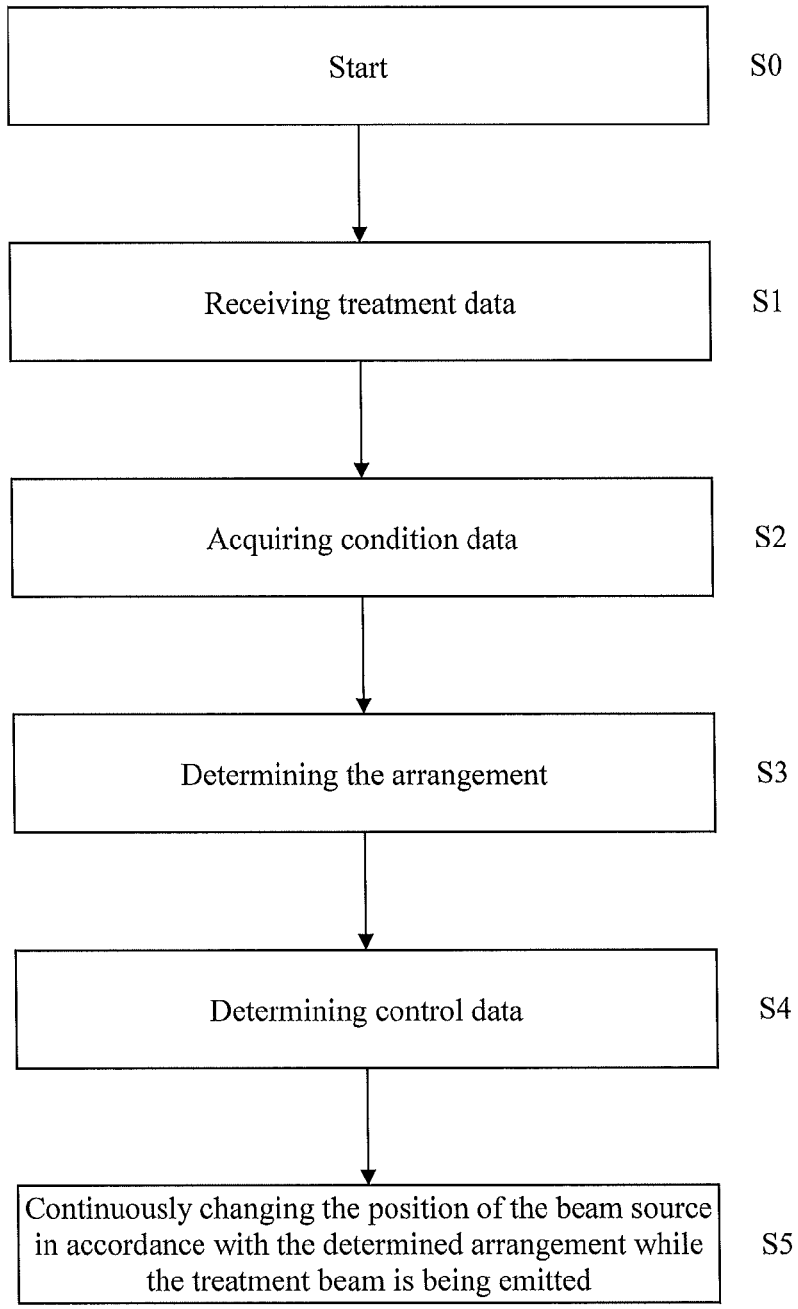
FIG. 6 shows a flow diagram of an embodiment of the method in accordance with the invention.

FIG. 6 shows a flow diagram of an embodiment of the method in accordance with the invention, wherein Steps S1 to S4 are part of the data processing method and Steps S1 to S5 are part of the beam position control method.

The method is started in a step S0, for instance by pressing a key on a keyboard of the computer 200. In a following step, the computer 200 receives treatment data, for instance via a line 216 which connects the monitoring devices 132 and 134 to the computer. The computer can then determine the position of the treatment body part on the basis of the data of the monitoring devices (by for instance matching these data to stored 3D data). The determined position (and/or geometry) of the treatment body part is then transmitted to the data processing method according to the invention and received by the data processing method of the present invention. Determining the position (and/or geometry) of the treatment body part can of course also be part of the data processing method of the present invention. The received treatment data in particular describe the position of the treatment body part relative to the treatment beam device (and, optionally, the geometry of the treatment body part). In particular, the position of the treatment body part can be described by a reference system which is defined by the aforementioned three axes X, Y and Z. The couch 10 is preferably controlled such that the treatment body part is situated at the origin of the aforementioned reference system.

In a following step S2, which however can of course also be performed before Step S1, the condition data are acquired. The condition data are for example acquired from a database of the computer 200. The condition data in particular describe constraints on the doses in body parts, in particular treatment body parts, specific body parts and other outside body parts. The condition data preferably describe the position and geometry of the outside body parts and specific outside body parts relative to the treatment body part. The condition data also preferably include information which describes possible continuous changes in the treatment beam positions during the treatment or which allows these to be determined. These possible changes in particular include changes in beam positions along a curved surface, i.e. such that the changes in beam positions from the starting point to the finishing point of the beam source movement preferably at least partly include a non-planar movement. This information can for instance be represented by data which describe the permitted independent and continuous rotations of the beam source about the axes X and Y. A continuous rotation about the axis Y is for example allowed over 360° from a starting point to a finishing point. A continuous rotation about the axis X is for example allowed between 30° and 330°, i.e. the angular range between 330° and 30° is not allowed, because the couch 10 blocks this rotation and the middle of the couch is for example situated at 0°.

In a following step S3, the arrangement of beam positions is determined on the basis of the condition data and the treatment data. As mentioned above, the determined arrangement is in particular non-planar, in order to optimally fulfil the conditions described by the condition data. The determined arrangements can be represented by a multiplicity of beam positions. Such a multiplicity of beam positions can in particular form a curved surface. In a following step S4, the control data for controlling the beam source movement in accordance with the determined arrangement are determined. In an additional step S5, the control data are transformed for example by an interface or a digital-analogue converter, into control signals for controlling motors of the beam source driver of the radiation treatment device 100. This driver causes the rotation of the beam source 120 about the X-axis and the Y-axis. The rotations about the X-axis and Y-axis are preferably performed at least partly simultaneously, such that the treatment beam source 120 follows a curved surface while the treatment beam is being emitted.

The invention claimed is:

1. A method for determining control data and controlling beam positions of a treatment beam for treating a treatment body part of an associated patient, the beam positions describing positions which a treatment beam has or would have if emitted by an associated beam source, said method being performed by a computer and comprising:

providing treatment data which comprises data on a position of the treatment body part;

providing condition data which describes constraints on the beam positions and/or constraints on positional changes of the beam positions, wherein said constraints allow for at least a part of the beam positions to lie not in a common plane;

providing an arrangement of the beam positions on the basis of the treatment data which arrangement fulfils the condition data;

determining control data for controlling a change of relative position between the beam source and the treatment body part, and for controlling an emission of the treatment beam from the beam source, the determined control data being configured to change the beam positions to follow the provided arrangement of the beam positions and to cause continuous emission of the treatment beam during a continuous change of the beam positions while the beam positions follow at least a part of the arrangement; and controlling the beam position by outputting control signals corresponding to the determined control data, wherein the condition data further describe at least one position of at least one specific outside body part, wherein the condition data include a condition according to which the arrangement is determined such that lines representing the treatment beam at the beam positions are arranged such that they lie in a virtual curved surface and such that following the arrangement results in a continuous undulating relative movement between the beam source and the treatment body part, wherein the relative movement occurs at least partly around the treatment body part, and according to which relative movement the beam source continuously emits the treatment beam during at least one or more parts of the continuous movement, the continuous undulating movement comprising a forward movement in one degree of freedom about a first axis and, during the forward movement about the first axis, a forward and backward movement in another degree of freedom about a second axis, the first and second axes passing through the treatment body part.

2. The method according to claim 1, wherein:

the condition data describe a radiation exposure condition describing conditions for the radiation exposure of outside body parts which are outside the treatment body part;

wherein the condition regarding the radiation exposure in outside body parts is or includes a condition according to which the dose in the at least one specific outside body part should be lower than in other outside body parts and/or lower than a first predefined dose value and/or only within a predefined percentage of the volume of the at least one specific outside body part higher than a second predefined dose value.

3. The method according to claim 1, wherein the step of providing an arrangement comprises:

a) providing candidate data which describe candidate arrangements; or b) providing candidate beam positions and determining candidate arrangements on the basis of the received candidate beam positions; and/or c) determining arrangements by using an optimization algorithm which determines an arrangement which optimally fulfils the conditions.

4. The method according to claim 1, wherein the providing the arrangement of beam positions comprises:

a) assessing the degree to which candidate arrangements fulfil the conditions, and selecting one arrangement out of a plurality of candidate arrangements on the basis of this assessment; or b) outputting assessment data which describe an assessment result and receiving selection data which describe a selected candidate arrangement; or c) selecting one arrangement out of a plurality of candidate arrangements to be the determined arrangement, on the basis of the condition data.

5. The method according to claim 1, wherein the condition data describe a radiation exposure in outside body parts which are outside the treatment body part and includes a condition that beam lines, which represent treatment beams at different beam positions and end in the treatment body part, are to be inclined with respect to each other if the beam lines hit the treatment body part on opposite sides.

6. The method according to claim 1, wherein the condition data include the condition according to which the arrangement is determined such that following the arrangement results in the continuous undulating movement of the beam source at least partly around the treatment body part.

7. The method according to claim 1, wherein the condition data comprise at least one of the following:
constraints on the geometry and/or position of an arrangement planning volume, said arrangement planning volume being a region within which the provided arrangement has to be confined;
constraints on the geometry of the treatment beam;
constraints on the acceleration and/or speed of positional changes in the treatment beam positions while following the arrangement; constraints on the dose rate of the treatment beam.

8. The method according to claim 7, comprising the steps of:
providing couch data which describe a planned position or a sequence of planned positions of a couch on which the patient is placed during treatment; and
determining the constraints on the geometry and/or position of the arrangement planning volume on the basis of the couch data and on the basis of couch volume data which describe a relationship between couch positions and the geometry and/or position of the arrangement planning volume.

9. The method according to claim 8, comprising:
providing candidate couch data which describe different candidate couch positions;
determining candidate arrangement planning volumes on the basis of the candidate couch data;
respectively determining an optimum arrangement for the different candidate arrangement planning volumes; and
selecting the best of the optimum arrangements.

10. The method according to claim 9, wherein the constraints on the geometry and/or position of the arrangement planning volume are described by:
a first angular range of allowed first rotational angles of treatment beam positions about the first axis which passes through the treatment body part; and/or
a second angular range of allowed second rotational angles of the treatment beam positions about the second axis which passes through the treatment body part; and/or
a third angular range of allowed third rotational angles of the treatment beam positions about a third axis which passes through the treatment body part,
wherein the determined control data are constituted to change the beam positions to follow the provided arrangement at least partly so that following the provided arrangement includes a simultaneous movement by a treatment beam source about at least two of the first, second and third axes during treatment.

11. The method according to claim 1, wherein:
the condition data describe a radiation exposure in outside body parts which are outside the treatment body part comprises a condition that the radiation exposure in the outside body parts is below a first threshold value; and/or
the condition data describe a radiation exposure in the treatment body part comprises a condition that the treatment beam passes through the treatment body part when following the arrangement and/or that the radiation exposure in the treatment body part is above a second threshold value.

12. The method according to claim 1, wherein:
the control signals comprise at least first and second sub-control signals for respectively and independently controlling at least a first and second sub-driver of a beam source driver,
wherein the beam source driver is designed to be able to drive the beam source in at least two degrees of freedom which are each independently controlled by the first and second sub-control signals transmitted to the first and second sub-driver while the beam source is controlled by the control signals so as to emit the treatment beam,
wherein the first sub-driver is designed to independently drive the beam source in a first degree of freedom, while the second sub-driver is designed to independently drive the beam source in a second degree of freedom, wherein the first and second degrees of freedom differ from each other.

13. A non-transitory computer readable storage medium storing a program for controlling beam positions of a treatment beam for treating a treatment body part of an associated patient, the beam positions describing positions which a treatment beam has or would have if emitted by a beam source, and which, when running on a computer or when loaded onto a computer, causes the computer to perform a method comprising:
providing treatment data which comprises data on a position of the treatment body part;
providing condition data which describes constraints on the beam positions and/or constraints on positional changes of the beam positions, wherein said constraints allow for at least a part of the beam positions to lie not in a common plane;
providing an arrangement of the beam positions on the basis of the treatment data which arrangement fulfils the condition data;
determining control data for controlling a change of relative position between the beam source and the treatment body part, and for controlling an emission of the treatment beam from the beam source, the determined control data being configured to change the beam positions to follow the provided arrangement of the beam positions and to cause continuous emission of the treatment beam during a continuous change of the beam positions while the beam positions follow at least a part of the arrangement;
and controlling the beam position by outputting control signals corresponding to the determined control data,
wherein the condition data further describe at least one position of at least one specific outside body part,
wherein the condition data include a condition according to which the arrangement is determined such that lines representing the treatment beam at the beam positions are arranged such that they lie in a virtual curved surface and such that following the arrangement results in a continuous undulating relative movement between the beam source and the treatment body part, wherein the relative movement occurs at least partly around the treatment body part, and according to which relative movement the beam source continuously emits the treatment beam during at least one or more parts of the continuous movement, the continuous undulating movement comprising a forward movement in one degree of freedom about a first axis and, during the forward movement about the first axis, a forward and backward movement in another degree of freedom about a second axis, the first and second axes passing through the treatment body part.

14. A computer comprising the non-transitory computer readable storage medium of claim 13.

15. A radiation treatment system, comprising:
a treatment beam source;
a beam source driver for changing a position of the treatment beam source in accordance with determined control data; and
a computer for determining the control data, the computer comprising a non-transitory computer readable storage medium storing a program for controlling beam positions of a treatment beam for treating a treatment body part of an associated patient, the beam positions describing positions which a treatment beam has or would have if emitted by the treatment beam source, and which, when running on the computer or when loaded onto the computer, causes the computer to perform a method comprising:
providing treatment data which comprises data on a position of the treatment body part;
providing condition data which describes constraints on the beam positions and/or constraints on positional changes of the beam positions, wherein said constraints allow for at least a part of the beam positions to lie not in a common plane;
providing an arrangement of the beam positions on the basis of the treatment data which arrangement fulfils the condition data;
determining control data for controlling a change of relative position between the beam source and the treatment body part, and for controlling an emission of the treatment beam from the beam source, the determined control data being configured to change the beam positions to follow the provided arrangement of the beam positions and to cause continuous emission of the treatment beam during a continuous change of the beam positions while the beam positions follow at least a part of the arrangement; and
controlling the beam position by outputting control signals corresponding to the determined control data,
wherein the condition data further describes at least one position of at least one specific outside body part,
wherein the condition data includes a condition according to which the arrangement is determined such that lines representing the treatment beam at the beam positions are arranged such that they lie in a virtual curved surface and such that following the arrangement results in a continuous undulating relative movement between the beam source and the treatment body part, wherein the relative movement occurs at least partly around the treatment body part, and according to which relative movement the beam source continuously emits the treatment beam during at least one or more parts of the continuous movement, the continuous undulating movement comprising a forward movement in one degree of freedom about a first axis, and, during the forward movement about the first axis, a forward and backward movement in another degree of freedom about a second axis, the first and second axes passing through the treatment body part,
wherein the computer is configured to control the beam positions of the treatment beam for treating the treatment body part of the associated patient by using the beam source driver, the treatment beam source, and motors which can be controlled independently.

\* \* \* \* \*